United States Patent [19]

Kulesh et al.

[11] Patent Number: 4,558,952

[45] Date of Patent: Dec. 17, 1985

[54] METHOD FOR MEASURING AN OPTICAL LENGTH OF LIGHT PATH AND A LASER INTERFEROMETER FOR CARRYING SAME INTO EFFECT

[76] Inventors: Vladimir P. Kulesh, ulitsa Stroitelnaya, 6, kv. 29; Leonid M. Moskalik, ulitsa Molodezhnaya, 13, kv. 177; Anatoly A. Orlov, naberezhnaya Tsiolkovskogo, 22, kv. 82, all of Zhukovsky, Moskovskaya oblast; Jury A. Bliznjuk, kvartal 3a, 25, kv. 102; Stanislav K. Shtandel, ulitsa Pervomaiskaya, 3/5, kv. 5, both of Lytkarino, Moskovskaya oblast, all of U.S.S.R.

[21] Appl. No.: 467,847

[22] Filed: Feb. 18, 1983

[51] Int. Cl.[4] .......................... G01B 9/02; G01B 11/02
[52] U.S. Cl. .................................. 356/349; 356/351; 356/352; 356/358
[58] Field of Search ............... 356/349, 351, 352, 358, 356/359, 360

[56] References Cited

U.S. PATENT DOCUMENTS 4,340,304 7/1982 Massie ............................ 356/349 X

OTHER PUBLICATIONS

Jacobs et al., "Measurement of Dimensional Stability" Final report Under Contract NAS8-28661, pp. 1-21, 7/75.
Lindborg Reichardt, Jenaer Rundschau, Journal No. 3, 1978, p. 137.
N. A. Massie, Applied Optics, 1980, pp. 154-160.
M. Born & E. Wolf, Principles of Optics, 1968, pp. 322-333.

Primary Examiner—Davis L. Willis
Assistant Examiner—Matthew W. Koren
Attorney, Agent, or Firm—Fleit, Jacobson, Cohn & Price

[57] ABSTRACT

A method for measuring an optical length of light path based on use of multiple-beam interference of light and carried into effect by forming an original light beam with two collinear components having mutually independent polarizations and different frequencies in such a manner that when forming each of the following interfering light beams from the preceding one, polarizations of the light components having different frequencies are mutually converted, whereupon the interfered light is converted into an electric signal and its phase is measured, by which the light path optical length is determined. A laser interferometer carrying said method into effect comprises: a laser and arranged consecutively along the direction of run of the light beam: a device for offsetting the frequency of one of the light components, reflecting elements, a polarizing element for separating the light of the interfering beams according to polarization, and a photoelectric converter of the interfered light into an electric signal, as well as a unit for measuring the phase of an electric signal, connected to the photoelectric converter and also a birefringent plate located between the reflecting elements and adapted for mutual conversion of polarizations of the two light components.

152 Claims, 27 Drawing Figures

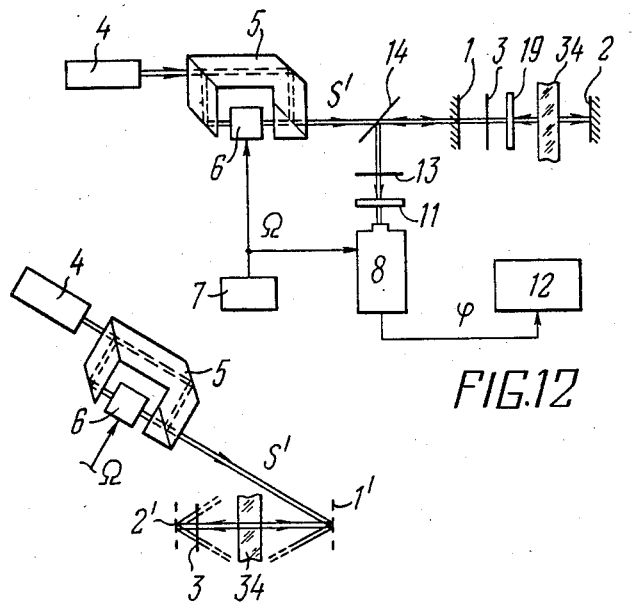
FIG.12
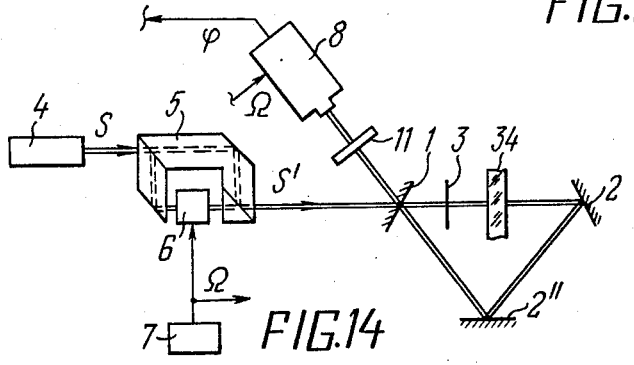
FIG.13a
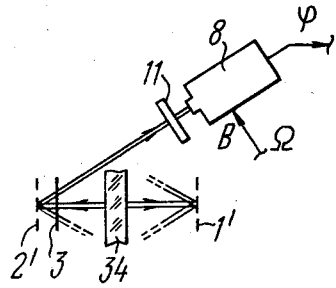
FIG.13b
FIG.14

METHOD FOR MEASURING AN OPTICAL LENGTH OF LIGHT PATH AND A LASER INTERFEROMETER FOR CARRYING SAME INTO EFFECT

The present invention relates generally to measuring techniques. More particularly the invention relates to methods for measuring an optical length of light path and to laser interferometers for carrying same methods into effect.

The invention can find extensive application in aerodynamics for studying gas density fields, when the gas flows along passageways or past a flying vehicle; in hydromechanics for investigating surface waves or flow of stratified liquids; in optics for checking the surface of optical elements for true shape and the various optical materials for homogeneity; in mechanics and mechanical engineering for determining geometrical parameters of items of diverse applications, their motions and deformation; and in many other fields of science and technology.

The invention can find most utility when applied for precision contactless automatic measurement of an optical length of light path or of any quantity unambiguously related with such length, in the presence of alien mechanical, acoustical, thermal, or some other effects.

An optical length $\delta$ of light path within an interval of a light ray is dependent both upon a geometric length l of this interval and upon the distribution of a refractive index n of the medium lengthwise the light ray within the interval involved.

$$\delta = 2\pi n l / \lambda, \qquad (1)$$

where $\lambda$ stands for an optical wavelength.

With known geometric length l of a light ray the result of measurement of an optical length $\delta$ of light path makes it possible to determine the mean value of the refractive index n within the entire light ray interval, which in turn allows of determining the average density of a liquid or gas, homogeneity of optical materials, chemical composition, etc., as well as distribution of these quantities in directions square with the light ray, and their variation with time.

With known distribution of the refractive index n of a medium, the optical length $\delta$ of light path being measured makes it possible to dertermine the geometric length l of the light ray interval, and may be adopted as a basis for determining the geometrical parameters of the item under investigation and its motion.

That is why the measurement of an optical length of light path proves to be an urgent though rather complicated problem of modern engineering.

Known in the art are many methods and devices for measuring an optical length of light path making use of diffraction, refraction, or interference effects, laser and holographic technology, electronics, and computer engineering.

Known in the present state of the art are Dvořák's and Teppler's shadow methods for detecting instability of an optical length of light path in the light beam cross-section (cf., e.g., "Homogeneity control of optical materials" by I. Reichardt, "Jenaer Rundschau" journal No. 3, 1978, p. 137 (in German). According to the Dvořák's method the medium under examination is put in between a small diameter light source and a screen. Variation of an optical length of light path from the light source to the screen in a direction square with the light ray causes the direction of light propagation to deflect. As a result, drops in light intensity occur on that portion of the screen which is located across the path of light that has passed through an optically inhomogeneous area. Such light intensity drops are in direct dependence upon the second derivative $\delta^2 \delta / \delta \rho^2$ of an optical length of light path with respect to a spatial coordinate $\rho = (x,y)$ in the light cross section. However, since precise numerical relationship between light intensity and an optical length of light path is too complicated to obtain, no numerical data can be derived through this method as such.

According to the Teppler's shadow method the light beam that has passed through the medium under examination, is focused until the image of the light source is obtained, then is converted until the image of the specimen under test appears on the screen. Optical filtration is carried out in the plane of the light source image. In a majority of cases an undistorted image of the light source is not allowed to pass to the screen, while the light rays deflected by optical inhomogeneity of the medium under test produce the image of such inhomogeneity on the screen in the form of a light contour against a dark background.

However, the method is sensitive to the first derivative of an optical length of light path with respect to a spatial coordinate, i.e., to the gradient grad $\delta$ of an optical length of light path across the light beam. The gradient value can be obtained semiquantitatively by placing a number of zonal light filters or many-aperture diaphragms in the plane of the light source image. Nevertheless, the accuracy of measurement by the Teppler's method is very low, while no quantitative investigation of an optical length of light path in homogeneous optical media is possible.

Some prior-art methods for measuring an optical length of light path are known which make use of interference of two light beams, of which one is let to pass through the medium under examination, while the other light beam, a reference one, is passed through another usually homogeneous medium having a known refractive index and a known geometrical length of light path through this medium. There are also known double-beam interferometers (Michelson's, Mach-Zehnder's, etc.) applied for carrying the aforesaid methods into effect (cf. A. A. Michelson, Amer.J.Sei., 22, 120, 1881; Phil.Mag., 13, 236, 1882, as well as L. Zehnder, Z.f.Instrkde, 11, 275, 1891; L.Mach, Z.f.Instrkde, 12, 89, 1892). The reference light beam that has passed through a certain known interval having a geometrical length $l_o$ in a medium having a known refractive index $n_o$, acquires a light wave phase delay equal to an optical length $\delta_o$ of light path along said reference interval $$\delta_o = \frac{2\pi n_o l_o}{\lambda}.$$

The measuring light beam thus acquires a phase delay equal to an optical length $\delta$ of light path within the measuring interval having a geometric length l in a medium with a refractive index n. Then the measuring and reference light beams are brought in coincidence with their wave-fronts. As a result, interference of the both light beams occurs, and an interference pattern is formed, featuring periodic distribution of light intensity $I(\rho)$ in a cross section of the interfering measuring and reference light beams. The periodic distribution is associated with the distribution of an optical length of light path across the measuring light beam $$\delta(\rho) = \frac{2\pi}{\lambda} n(\rho) l(\rho),$$

by the following relation:

$$I(\rho) = I_o(\rho)\{1 + \cos[\delta(\rho) - \delta_o]\},$$

where:

ρ is the radius-vector of the coordinates of points in a cross section of the interfering light beams;

$I_o(\rho)$ is the distribution of average light intensity of the interference pattern.

The interference pattern is in fact a set of alternating dark ($I(\rho)=0$) and light ($I(\rho)=2I_o(\rho)$) interference bands, which are in effect the lines of equal values $\delta_N(\rho)$ of an optical length of light path of the measuring light beam $$\delta_N(\rho) = \delta_o - \pi N = \text{const}, (N=0, \pm 1, \pm 2 \ldots)$$

The aforedescribed methods and double-beam interferometers suffer from a number of disadvantages common to them:

uncertainty in the sign of change of a difference between the optical lengths of light path of the measuring and reference light beams;

complicated labourious lengthy decoding of an interference pattern due to photographic recording of such an interference pattern followed by decoding said pattern, which is carried out "manually" in a majority of cases, that is, by visually counting the interference bands;

low measuring accuracy due to necessity for light intensity measurement in an interference field, or for measurement of photographic density of an interferogram, since both of them are badly affected by nonuniformity and instability of the light source, soiled optical system of an interferometer, any flaws of photographic materials, such as coarse-grained emulsion, non-linear characteristics, etc., as well as by the effect of the human factor involved in manual decoding of an interferogram;

necessity to provide a known value of the optical length $\delta_o$ of light path of the reference light beam and ensure its invariability in the reference light beam cross-section and constancy in time, especially when measurement is carried out under conditions of heavy extraneous vibrations, acoustic disturbances, variations of ambient parameters (temperature, pressure, density), air streams, and so on;

complicated and highly expensive optical systems of double-beam interferometers capable of adequately stable and consistent measurement, especially those intended for studying big fields.

Another method for measurement of an optical length of light path is known to occur by way of interference of two beams of coherent light, i.e., a measuring and a reference, the optical frequency of one of these beams being shifted by a present value of $\Omega$, which lies in the radio-frequency range. Upon recording an interference pattern the interfered light is subjected to photoelectric conversion, the phase of a variable component of the resulting electric signal is measured, and an optical length of light path in the measuring light beam is judged by the measured value of the above-mentioned phase. There is also known a laser interferometer for carrying the afore-described method into effect (cf., e.g., N. A. Massie, Applied Optics, 19, 1, 1980, pp. 154–160).

The essence of the method and of the interferometer operation resides in that a two-component coherent light beam is established with the help of a laser and an optical frequency modulator, the optical frequency of one of said light beams is shifted with respect to the optical frequency ω of the other light beam by a preset value of $\Omega$, the aforesaid different-frequency beam components are separated into a reference and a measuring beam, the measuring beam is passed along the path interval under examination, while the reference light beam is let to pass along a light path interval having a known optical length $\delta_o$, whereupon both light beams are integrated. As a result of interference of the two light waves having different frequencies ω and ω+$\Omega$ and different phases $\delta_o$ and $\delta(\rho)$, an interference pattern is formed, the light intensity of which at each point ρ is described by the following expression:

$$I(\rho, t) = I_o(\rho)\{1 + \cos[\Omega t - (\delta(\rho) - \delta_o)]\},$$

where t denotes time.

As is evident from the above-stated expression, an electric signal produced by virtue of photoelectric conversion of light at the point in question, has a variable component with a frequency $\Omega$ equal to a difference between the frequencies ω and ω+$\Omega$ and a phase equal to a difference between the phase $\Delta\delta = \delta(\rho) - \delta_o$ of the interfering light beams.

Such a method dispenses with photographic recording and subsequent decoding of the interference pattern, and the result of measuring the phase of an electric signal obtained in a numerical code can be displayed on a digital indicator, or be directly inserted into a computer for processing in real time and putting under storage. The accuracy of measuring the phase of an electric signal by radiophasometric means is very high and, since the measurement is carried out automatically, no human factor is involved, which also contributes to more precise and reliable information on an optical length of light path. The method is sensitive to the reversal sign of an optical length of light path.

However, both the method and the interferometer described above suffer from the disadvantages inherent in the double-beam interferometers. The disadvantages reside in a complicated and highly expensive optical system, provision of necessary stability and immunity to disturbances, especially under arduous conditions involving mechanical, acoustic, thermal, or some other adverse effects.

One more method for measuring an optical length of light path known heretofore involves multiple-beam interference, wherein a coherent light beam is established from which a number of interfering beams are formed so that each of the following interfering beams is formed by separating part of the light of a preceding interfering light beam and by passing the separated part of light along the same path interval under examination. Thereupon a resultant interference pattern is registered (cf., e.g., M. Born, E. Wolf, Principles of Optics. Pergamon Press, 1968).

As a rule, such a light interval is confined within two reflecting elements having a reflection factor less than a unity. The beam of coherent light, on having passed through the first reflecting element, runs along a preset path interval to the second reflecting element and acquires a phase delay δ equal to the desired optical length of light path within this interval. Part of the light having the phase delay δ passes through the second reflecting element, while the other part of the light is reflected and runs back along the preset path interval to the first reflecting element, thus acquiring an additional phase delay δ. Part of the light having yet the phase delay equal to 2δ, emerges through the first reflecting element, while the remaining part of the light is reflected to run again along the preset path interval to the second reflecting element, thus acquiring the phase delay equal to 3δ. Then part of the light emerges through the reflecting element, while the other part is reflected to perform a next run along the preset path interval to the first reflecting element and backwards, acquiring an additional phase delay equal to 2δ at each run. A large number of interfering light beams go beyond the preset path interval between the reflecting elements on the side of both the first and second elements, the phases of these light beams differing from each other by 2δ consecutively in the sequence of separation of the light beams, while their amplitudes diminish in geometric progression. Relationship between the interfered light and an optical length of a preset light path interval is expressed by a non-sinusoidal periodic function having a period $\Delta\delta = 2\pi$, an integral number of periods, that is, the order of interference $D = \text{int}(\delta/2\pi)$ being equal to an integral number of optical wavelengths $\lambda/n$ within a preset interval, while the light intensity variation within the period, i.e., the shape of the interference fringe contour represents the fractional part d of this value of the light path optical length:

$$\delta = 2\pi(d+D). \qquad (2)$$

According to the aforedescribed method for measuring an optical length of light path every interfering light beam runs through the same optical path, and no additional reference light beam passing along another optical path is required. Therefore, unlike the methods utilizing the double-beam interference technique the method in question is free from any measuring errors resulting from determination error or due to instability of an optical length of the reference light beam path. All this simplifies the measurement process and the interpretation of the results obtained.

However, the order of interference and the contour of the interference fringe are determined, when measuring the integral and fractional parts of the value of the light path optical length, either by visually counting the number of interference fringes or by photometric measurement of the interference pattern or of its photographic image, i.e., an interferogram. In the former case errors due to human factor are inevitably involved, while in the latter case errors are inescapable due to fluctuation noise of photoelectric current and variations of the interfered light intensity caused by the aforelisted extrinsic factors. This results in too low accuracy and reliability of measurement of the light path optical length.

Moreover, the determination accuracy of the fractional part is low due to a complicated nonsinuosidal shape of the interference fringe contour, whereby the measured intensity of the interfered light is widely variable when the value of the light path optical length features but slight deviation from an integer, and remain practically unaffected within a greater portion of the interference fringe. However, it is on this portion of the interference fringe that the intensity of the interfered light and the light path optical length cannot be identified. This in turn affects adversely the accuracy of measurement of the fractional part of the aforesaid value.

Furthermore, the known method under consideration is insensitive to the reversal sign of the light path optical length, which restricts much the capabilities of the method when measuring the distribution of the light path optical length in a cross section of the interfering light beams or in the case of variation of said length with time.

In addition, decoding of interferograms obtained by the multiple-beam inference technique is in fact no less sophisticated, labourious and lengthy than in the case of the double-beam interferometry.

Most proximate, as to its physical essence, to the interferometer proposed in this invention, is the Fabry-Perot or Fiseau-type interferometer, incorporating a source of coherent light, two reflecting elements set one against the other on the optical axis of said coherent light source, and a photorecorder for registering the obtained interference pattern (cf. C. Fabry, A. Perot, Ann. Chim. Phys., 16, 115, 1899).

However, the interferometer described above suffers from every disadvantage inherent in the known method for an optical length of light path using the multiple-beam interference technique.

In addition, the known laser interferometer does not allow automation of the process of measuring the light path optical length mostly due to low immunity to disturbances when measuring the intensity of the interfered light, uncertainty in the sign of change of light intensity versus the sign of change of the light path optical length being measured, low signal-to-shot noise ratio when studying the distribution of the light path optical length over a large sectional field of the interfering light beams at high spatial resolution.

It is a primary and essential object of the present invention to provide such a method for measuring an optical length of a light path interval that would be capable of high-accuracy measurement due to application of the multiple-beam interference technique.

It is another object of the present invention to provide such a method for measuring an optical length of a light path interval that would make it possible to directly measure an optical length of a preset interval without application of an additional reference light path interval.

It is one more object of the present invention to provide a method capable of carrying out immediate conversion of a desired optical length of a preset interval into a numerical code.

It is still more object of the present invention to provide a method for measuring an optical length of a light path interval, which would be instrumental in attaining much higher noise immunity of measurement.

It is yet still more object of the present invention to provide a method for measuring an optical length of a preset light path interval in real time.

It is also an object of the present invention to provide a method for measuring variation of an optical length of light path with time.

It is a further object of the present invention to provide a method for measuring the distribution of an optical length of light path over a cross-section of the interfering light beams.

It is still further object of the present invention to provide a method for measuring an optical length of a preset light path interval, which would be capable of determining the sign of change of light path optical length.

It is yet still further object of the present invention to provide a method for measuring an optical length of a preset light path interval, which would be capable of measuring a complete optical length of light path, including an integral and a fractional part of the optical wavelength.

It is an additional object of the present invention to provide a method which would allow for a possibility of stabilizing a preset optical length of light path interval.

It is another additional object of the present invention to provide a method would make it possible to control the process governing the variations of the light path optical length.

It is another primary and essential object of the present invention to provide a laser interferometer, wherein higher noise immunity and a greater degree of automation of the process of measuring light path optical length would be attained due to establishing two light components having different frequencies and converting the interfered light into an electric signal.

It is one more object of the present invention to provide a laser interferometer, wherein high accuracy of measuring an optical length of light path and of converting the measuring results into a numerical code would be attained due to accurate measurement of the phase of an electric signal.

It is a further object of the present invention to provide a laser interferometer, wherein measurement of an optical length of light path would be made possible within a light path interval shaped as a closed polygon with the use of at least three reflecting elements.

It is still further object of the present invention to provide a laser interferometer, wherein stabilization of a preset light path interval and control over the processes governing an optical length of light path within a preset interval would be attained due to presetting a certain phase value and comparing said value with the measured value.

It is yet still further object of the present invention to provide a laser interferometer, wherein distribution of an optical length of light path across the interfering light beams would be attained due to expanding the original beam and converting the light into electric signals at different points of the interference pattern.

It is an additional object of the present invention to provide a laser interferometer, wherein visual observation of the interference pattern would be ensured simultaneously with measuring the distribution of light path optical length due to separation of a part of light of the interfering light beams and by virtue of pulse modulation of the light intensity.

It is likewise an object of the present invention to provide a laser interferometer, wherein an integral and a fractional part of an optical length of a light path interval would be measured by forming a light beam having different wavelengths.

It is still one more object of the present invention to provide higher stability and performance characteristics of the laser interferometers developed, due to the use of a maximally simple interference unit.

It is yet still one more object of the present invention to provide reduced costs of the laser interferometers developed, due to a minimized number of top-quality optical elements for the interference unit.

It is an additional object of the present invention to render the laser interferometers developed more adaptable to manufacture due to unified units applied.

It is also an object of the present invention to provide multipurpose laser interferometers due to their being fitted with a greater number of change units.

The aforesaid and other objects are attained due to the fact that in the method of the invention for measuring an optical length of a light path interval, consisting in that a coherent light beam is created, from which a number of interfering light beams are formed in such a manner that each of the next interfering beams is formed by separating part of the light of a preceding interfering light beam and by passing the separated part of light along the same path interval, whereupon the interfering light beams are brought in coincidence and the resultant interference pattern is recorded, according to the present invention, the coherent light beam established has two collinear components featuring different independent polarizations, the optical frequency of one of said components is offset with respect to that of the other component, in each pair of the light components, when forming every next interfering light beam from the preceding one, polarization of one of the light components is converted into polarization of the other component, and polarization of the other component is converted into polarization of the former component, upon coinciding the interfering light beams their light is divided into two beams featuring the aforesaid independent polarizations, and upon recording the interference pattern, the interfered light of each of the two independent polarizations is subjected to photoelectric conversion separately, after which the phases of the resultant electric signals are measured, whereby the light path optical length within said interval is judged.

This makes it possible, using the multiple-beam interference technique, to convert information on the desired light path optical length within a preset interval, with a high degree of accuracy, directly into a numerical code and to process said information in real time.

It is expedient that the aforesaid mutual conversion of polarization of a pair of the light components be followed by suppression of the light having one of said polarizations and that photoelectric conversion of the interfered light be carried out with the other of said polarizations.

This allows of enhancing the linearity of conversion of the desired light path optical length into a numerical code, which adds more to the measurement accuracy.

It is practicable to register changes in the measured phases of the variable components of the resultant electric signals with time so that variations of the light path optical length can be determined from the variations of the measured phases.

This makes it possible to measure variations of the light path optical length with time and thereby to study how the processes characterized by variations of the light path optical length proceed in time.

Photoelectric conversion of the interfered light can be performed at no less than two points on an interference pattern and the distribution of the light path optical length across the interfering light beams can be judged by the results of measurement of the phase of electric signals obtained at these points.

This makes it possible to measure the distribution of the light path optical length across the interfering light beams and thereby to study the distribution of physical quantities characterized by an optical length of the path of light interacting therewith.

It is expedient to measure the differences between the phases of electric signals resultant from photoelectric conversion of the interfered light beams at different points of the interference pattern so that the gradients of the light path optical length across the interfering light beams can be determined from said phase differences.

This makes it possible to detect inhomogeneities of physical quantities within the field of the object under study.

It is practicable to preassign the phase value of at least one electric signal to which corresponds at least one known value of the light path optical length, to vary the optical length of a preset light path interval and, when the measured phase of a signal obtained at least one point of the interference pattern has reached one of the preassigned phase values, to register the value of the aforesaid variation of the optical length of the light path interval, whereupon the desired optical length of the preset interval could be determined at a corresponding point of the cross section of the interfering light beams by subtracting the registered value of the optical length variation from the known value of the light path optical length.

This makes it possible to increase the sensitivity and accuracy of measurement of the light path optical length, to stabilize and automatically control the optical length of a preset interval, as well as physical quantities and processes characterized by the light path optical length.

It is favourable to define a coherent light beam having a known wavelength and to measure the phases of the respective electric signals, whereupon it is practicable to vary at least once the wavelength of the coherent light also by a known value and then to measure again the phases of the respective electric signals, after which the light path optical length can be judged by the ratio of the phase values measured at different known light wavelengths.

This makes it possible to determine an integral and a fractional part of the optical length of a preset light path interval by a series of consecutive measurements.

When forming a coherent light beam, the light may be established having at least two known wavelengths, photoelectric conversion of the interfered light may be applied to each of the known wavelength separately and the phases of the respective electric signals may be measured, whereupon the light path optical length can be judged by the ratio of the phase values measured at different known light wavelengths.

This makes it possible to determine an integral and a fractional part of the varying light path optical length on the predetermined instants.

The aforesaid and other objects are also attained due to the fact the laser interferometer of the invention, comprising a laser, at least two reflecting elements placed one after the other as along the run of the light beam and adapted for preassigning a light path interval and for forming and coinciding the interfering light beams, and a photorecorder of the interference pattern obtained, according to the present invention, incorporates a device for separating two collinear light components with independent polarizations and a device for shifting the light frequency of one of said components with respect to that of the other component, both of said devices being placed in between the laser and the reflecting elements, a master oscillator connected to the light-frequency shifting device, a birefringent plate positioned between the reflecting elements, and a polarizing element set on an optical axis of the interfered light before the photorecorder which is in fact a photoelectric converter of the interfered light, and an electric-signal phase measuring unit connected to said photoelectric converter.

Such an interferometer makes it possibe to measure the light path optical length over an interval preassigned by the reflecting elements with a high degree of accuracy and to automate the measurement process at a maximally simple construction of the interference unit.

It is expedient that the aforesaid device for separation of the light components would be capable of separating the light components having circular polarizations which feature opposite directions of rotation of the electric field vector.

This enables the light path optical length being measured to be converted into a numerical code in a most simple way.

It is reasonable that the laser interferometer would comprise a quarter-wave plate placed across the path of the interfered light before the polarizing element, and that the aforesaid device for separation of the light components would separate the light components featuring linear mutually square polarizations.

This allows the provision of the interferometer having extended process capabilities.

It is favourable that the laser interferometer would comprise a beam-splitter element for separating the interfering light beams reflected from the reflecting elements, said beam-splitter element being placed between the light frequency shifting device and the reflecting elements and that the aforesaid polarizing element and photorecorder be positioned past said beam-splitter element as along the run of the reflected interfered light.

This makes it possible to attain better arrangement of the interferometer and to extend the field of its application, e.g., for examination of opaque objects.

The aforementioned device for separation of the light components is capable of separating the light components featuring linear mutually square polarizations.

This allows the light path optical length being measured to be converted into a numerical code in a most simply way when examining opaque objects.

It is recommendable that the laser interferometer would comprise a quarter-wave plate put across the path of the interfered light before the polarizing element and that the aforesaid device for separation of the light components would separate the light components featuring circular polarizations which have opposite directions of rotation of the electric field vector.

This makes it possible to extend the field of application of the laser interferometer to, for example, examination of objects possessing optical anisotropy.

A double-frequency laser based upon the Zeeman effect may be utilized as the laser of the device for separation of the light components featuring circular polarizations and of the device for shifting the light frequency of one of the separated components.

This enables one to simplify the units intended for forming the original beam of coherent light and the construction of the interferometer as a whole.

The device for separation of the light components having linear polarization is practicable to be made as a dual-beam polarization interferometer one of whose arms mounts the light frequency shifting device.

This contributes to unification of the interferometer units, reduces its cost and renders it more adaptable to manufacture.

The light frequency shifting device may be in effect an electrooptic frequency modulator.

This also conduces to unification of the interferometer units, cuts down its cost and makes it more adaptable to manufacture.

The light frequency shifting device may be essentially an acousto-optic frequency modulator.

This is likewise conducive to unification of the interferometer unification, to lower cost and higher adaptability of the interferometer to manufacture.

The laser interferometer may comprise a polarizer placed in between the reflecting elements past the birefringent plate.

This makes it possible to better the linearity of conversion of the light path optical length into a numerical code.

The aforesaid polarizing element may be in effect a polarizer.

This enables the light of the interfering beams to be split as to polarization.

The polarizing element may be essentially a polarization beam-splitter adapted for dividing a light beam into two beams featuring linear mutually square polarizations, while the photorecorder may be made as two photoelectric converters connected to the phase measuring unit, one of said converters being arranged on an optical axis of one of the two divided light beams, and the other converter is located on an optical axis of the other light beam.

This makes it possible to enhance light utilization efficiency and to render the interferometer twice as more sensitive, which adds to higher economy of the interferometer and improved accuracy of measurement.

The aforementioned reflecting elements may be installed within a predetermined interval one against the other on a common axis, while the birefringent plate may be in essence a quarter-wave plate.

This makes it possible to form the interfering light beams in a simplest way and to preassign the light path interval.

At least three such reflecting elements are practicable to be set at the corners of a closed polygon, which is in fact a preset light path interval.

This enables the capabilities of the interferometer to be extended to measurement of the light path optical length on a nonstraight-line path.

The birefringent plate may be in effect a half-wave plate.

This allows the polarizations of the light components to be converted in a simplest way.

The reflecting elements may be fashioned as partially reflecting mirror surfaces.

This enhances adaptability of the interferometers to manufacture and reduces their costs.

At least one of the reflecting elements may be in essence a diffraction grating so positioned that the axis of the light beam of one of the diffraction orders of said grating should align with the axis interconnecting the adjacent reflecting elements.

This contributes to extended process capabilities of the interferometer.

It is appropriate that the birefringent plate be located nearby the diffraction grating and that a difference between the shifts of the light wave phases in two working diffraction orders be equal to a quarter wavelength.

This makes it possible to provide in a simplest way, conversion of the polarizations of the light components in the case of diffraction gratings employed as the reflecting elements.

The diffraction grating may be made as a hologram.

This makes it possible to make the interferometer more adaptable to manufacture and less expensive, as well as to provide a possibility of compensating for the distribution of the light path optical length.

The laser interferometer may incorporate an optical system adapted for expanding the light beam and placed before the reflecting elements.

This is instrumental in attaining the required cross-sectional dimensions of the interfering light beams when measuring the distribution of the light path optical length in the aforesaid cross section.

It is practicable that the photoelectric converter be provided with an interference pattern scanning device.

This makes it possible to measure the distribution of the desired light path optical length by successively moving the photoelectric converter through the preset points of a light beam cross-section.

The laser interferometer may comprise an optical element adapted for separating part of the light of the interfering beams and located before the photorecorder, and an additional photorecorder located on an optical axis of the separated light beam.

This makes it possible to record fluctuations and unequality of the wave phase of the original light beam and to allow for the changes in the distribution of the desired optical length of a light path interval common to the entire interference pattern.

The photoelectric recorder may be in fact a single quadratic photodetector.

This enables photoelectric conversion of an optical signal into an electric one to be performed in a simplest way.

The photoelectric converter may be provided as a photodetector array made up of a number of photodetectors connected to the phase measuring unit through a switching device.

This ensures simultaneous conversion of an optical signal into an electric one at a number of points of the cross-section of the interfering light beams.

The photoelectric converter may also be fashioned as a photodetector array made up of a number of photodetectors each of which is connected to its own phase measuring unit.

It is due to the aforesaid feature that the light path optical length can be measured simultaneously at a number of points across the section of the interfering light beams.

At least one of the photodetectors of the additional photorecorder may be connected likewise to at least one of the phase measuring unit of the main photorecorder.

This makes it possible to compensate for fluctuations of the wave phase of the original light beam occurring at preset points of the cross-section of the interfering light beams.

The laser interferometer may comprise a device for displacing the light beam parallel to itself in two mutually square directions, said device being situated before the reflecting elements.

This makes it possible to increase light utilization efficiency, to attain a higher electric signal-to-shot noise ratio and to ensure equally accurate measurement across the entire cross-section of the interfering light beams.

The aforementioned light beam displacing device may be linked up with the interference patter scanning device.

This feature enables the operation of an interferometer with such a scanning device to be more reliable.

The aforesaid light beam displacing device may be linked up with the switching device.

This makes it possible to increase the operational reliability of an interferometer using a photodetector array.

The laser interferometer may incorporate at least one device for control of an optical length of the light path interval, comprising a transducer of light path interval optical length alteration, said device being positioned in between the reflecting elements, a unit for presetting the phase values corresponding to the known values of the light path optical length, a phase comparator unit whose inputs are electrically connected respectively to the phase value presetting unit and to at least one own phase measuring unit, while the output thereof is connected to at least one of the aforedescribed light path interval optical length control device, and a computer device electrically connected to the transducer of light path interval optical length alteration and to the phase value presetting unit.

This makes it possible to extend the functional capabilities and field of application of the laser interferometer, particularly in systems of automatic control of processes affecting the light path optical length.

The laser interferometer may comprise a light intensity modulator installed before the additional photorecorder, and a generator of electric pulses electrically connected to the light indensity modulator, while the additional interference pattern photorecorder may be in the form of an image recorder.

This extends the functional capabilities of the laser interferometer, renders it more versatile, in particular, enables one to observe and record an interference pattern concurrently with measuring the light path optical length.

It is expedient that the generator of electric pulses be electrically connected to the master oscillator and be time-locked with it as to pulse repetition frequency.

This facilitates the tuning of the laser interferometer and its practical application due to a possibility of visual observation of the interference pattern obtained.

The source of coherent light may have a tunable wavelength.

This enables an integral and a fraction part of the light path optical length to be determined.

The laser interferometer may comprise an optical unit for splitting the interfered light beam into a number of separate beams depending upon their wavelengths, which is placed past the polarizing element, and each of said separate light beams may have its own photorecorder of interference pattern arranged on an optical axis of each light beam, while the coherent light source emits light featuring at least two known wavelengths.

This makes it possible to determine an integral and a fractional part of the light path optical length when studying the processes proceeding in time.

In what follows the invention will now be disclosed in specific exemplary embodiments thereof given by way of illustration with reference to the accompanying drawings, wherein:

FIG. 12 is a block-diagram of one of the practicable embodiments of the laser interferometer using reflected light and featuring suppression of the light having one of the independent polarizations, according to the invention;

FIG. 13A illustrates an embodiment of the reflecting elements made as diffraction gratings and shows how the original light beam is admitted at a diffraction angle to one of the diffraction gratings, according to the invention;

FIG. 13B illustrates an embodiment of the laser interferometer, wherein the photorecorder is placed on the axis of one of the diffracted light beams, according to the invention;

Figure 1:
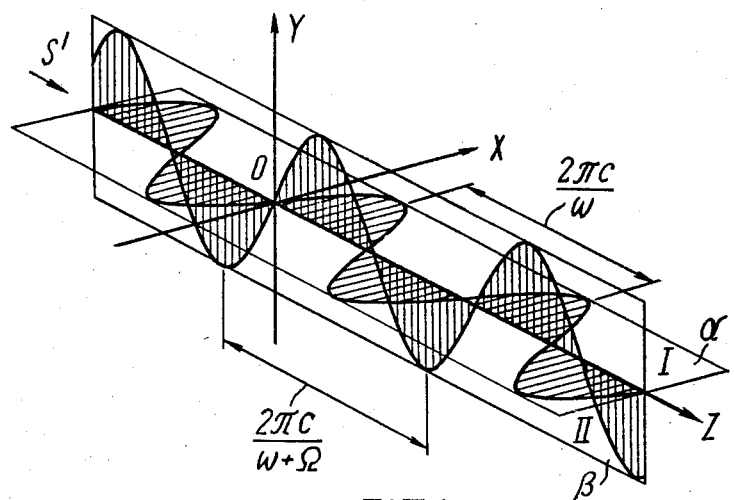
FIG. 1 is a schematic view of the configuration of an electric field of two separated components I and II of the original light beam featuring polarizations $\alpha$ and $\beta$ and frequencies $\omega$ and $\omega + \Omega$, according to the invention.

FIG. 14 is a schematic view of one of the embodiments of the laser interferometer, wherein a preset light or circular polarizations $\alpha°$ and $\beta°$ featuring opposite directions of rotation of the electric field vector). Then the light frequency of one of the separated components, e.g., the component II is offset with respect to the light frequency $\omega$ of the other component I by the value of $\Omega$.

The thus-formed original light beam $S'$ described by the vector $\vec{e_s}$, is directed along the axis OZ onto the reflecting surfaces of the reflecting elements 1 and 2, said reflecting surfaces having amplitude reflection factors $r_1$, $r_2$ and amplitude transmission factors $\tau_1$, $\tau_2$, respectively ($\tau_1^2 + r_1^2 = 1$; $\tau_2^2 + r_2^2 = 1$).

Upon multiple reflection of light from the reflecting elements 1 and 2 in the directions of the transmitted and reflected light, two rows of interfering light beams are formed. As the light beam passes through a section, wherein a birefringent plate 3 is situated, the linear polarizations are each time conversed into the circular ones, and the circular polarizations, into the linear ones.

A number of interfering beams having linear polarizations $\alpha^1$ and $\beta^1$ are formed in the direction of reflected light; said beams being represented in Table 1 below.

TABLE 1

| No. of light beam | Relative amplitude | Phase factor | Light frequency of beam component having polarization | |
|---|---|---|---|---|
| | | | $\alpha'$ | $\beta'$ |
| 1 | $r_1$ | 1 | 1 | $e^{-i\Omega t}$ |
| 2 | $\tau_1^2 r_2$ | $e^{-i2\delta}$ | $e^{-i\Omega t}$ | 1 |
| 3 | $\tau_1^2 r_2(r_1 r_2)$ | $e^{-i4\delta}$ | 1 | $e^{-i\Omega t}$ |
| 4 | $\tau_1^2 r_2(r_1 r_2)^2$ | $e^{-i6\delta}$ | $e^{-i\Omega t}$ | 1 |
| ... | ... | ... | ... | ... |
| j | $\tau_1^2 r_2(r_1 r_2)^{j-2}$ | $e^{-i2(j-1)\delta}$ | 1 (j-odd number) $e^{-i\Omega t}$ (j-even number) | $e^{-i\Omega t}$ (j-odd number) 1 (j even number) |
| ... | ... | ... | ... | ... |

And in the direction of light transmitted through the surface of the reflecting elements 1 and 2 there are formed a number of beams having circular polarizations $\alpha_o$ and $\beta_o$ and represented in Table 2 below.

TABLE 2

| No. of light beam | Relative amplitude | Phase factor | Factor representing light frequency having polarization | |
|---|---|---|---|---|
| | | | $\alpha^o$ | $\beta^o$ |
| 1 | $\tau_1 \tau_2$ | $e^{-i\delta}$ | 1 | $e^{-i\Omega t}$ |
| 2 | $\tau_1 \tau_2(r_1 r_2)$ | $e^{-i3\delta}$ | $e^{-i\Omega t}$ | 1 |
| 3 | $\tau_1 \tau_2(r_1 r_2)^2$ | $e^{-i5\delta}$ | 1 | $e^{-i\Omega t}$ |
| 4 | $\tau_1 \tau_2(r_1 r_2)^3$ | $e^{-i7\delta}$ | $e^{-i\Omega t}$ | 1 |
| j | $\tau_1 \tau_2(r_1 r_2)^{j-1}$ | $e^{-i(2j-1)\delta}$ | 1 (j-odd number) $e^{-i\Omega t}$ (j-even number) | $e^{-i\Omega t}$ (j-odd number) 1 (j-even number) |

The interfering beams are mixed together on both sides of a preset interval. Then the light of the mixed beams is divided according to independent polarizations: the light of the mixed reflected beams is divided into beams $\epsilon_\alpha'$ and $\epsilon_\beta'$ having linear orthogonal polarizations, while the light of the mixed transmitted beams is divided into beams $\epsilon_\alpha°$ and $\epsilon_\beta°$ having opposite circular polarizations. In each of the newly formed beams multiple-beam interference of the light of a number of beams occurs, of which each next beam differs from the preceding one in the light wave phase delay equal to the doubled optical length $2\delta$ and in the frequency which assumes alternatively the values of $\omega$ and $\omega + \Omega$. The intensity $I = \epsilon \cdot \epsilon^*$ of the interfered light depends upon time t and optical length $\delta$ of the light path within a preset interval:

The intensity values $I_\alpha°$ (t,$\delta$) and $I_\beta°$ (t,$\delta$) of the respective components of the transmitted light beams take the following form:

$$I_\alpha°(t,\delta) = A(\delta) + B(\delta) \cos[\Omega t + 2\delta + \Phi(\delta)];$$

$$I_\beta°(t,\delta) = A(\delta) + B(\delta) \cos[\Omega t - 2\delta - \Phi(\delta)]. \quad (3)$$

The intensity values $I_\alpha'$ (t,$\delta$) and $I_\beta'$ (t,$\delta$) of the respective components of the reflected light beams assume the following form;

$$I_\alpha'(t,\delta) = 1 - A(\delta) - B(\delta) \cos[\Omega t + 2\delta + \Phi(\delta)];$$

$$I_\beta'(t,\delta) = 1 - A(\delta) - B(\delta) \cos[\Omega t - 2\delta - \Phi(\delta)]. \quad (3')$$

Figure 3:
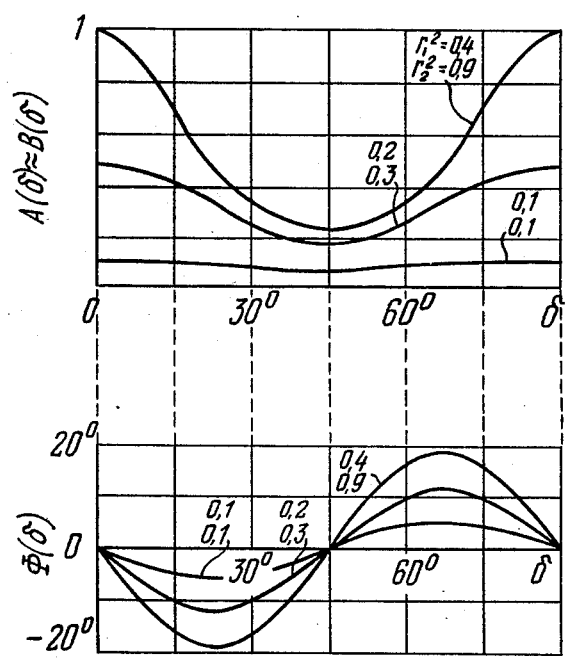
FIG. 3 illustrates graphic representation of the relationship of a light path optical length $\delta$ and a "constant" component A ($\delta$), the amplitude of a variable component B ($\delta$) and phase distortions $\Phi$ ($\delta$) of an electric signal resulting from measurement, according to the invention.

The values of $A(\delta)$, $B(\delta)$ and $\Phi(\delta)$ are in fact the periodic functions of an optical length $\delta$ of light path depending parametrically upon the reflection factors $r_1$ and $r_2$ of the surface of the reflecting elements 1 and 2. FIG. 3 represents graphic plots of the values of $A(\delta)$, $B(\delta)$ and $\Phi(\delta)$ as a function of $\delta$ at various values of $r_1$ and $r_2$.

The intensity values of $I_\alpha°$, $I_\beta°$, $I_\alpha'$ and $I_\beta'$ of the interfered light in each of the beams are converted into electric signals. The "constant" component of an electric signal is proportionate to $A(\delta)$, the amplitude of the variable component is proportional to $B(\delta)$, while the phase of the variable component is equal to $$\phi = 2\delta + \Phi(\delta). \quad (4)$$

It ensues from Eqns (3) and (3'), as well as from the graphic representations in FIG. 3 that with low values of the reflection factors $r_1$ and $r_2$ the "constant" component and the amplitude of the variable component of an electric signal remain almost unaffected with variation of $\delta$. The "constant" component of the reflected light approximates the signal amplitude, i.e., the modulation depth of an electric signal approximates unity. On the other hand the "constant" component of the transmitted light is much greater than the signal amplitude, whence the depth of the signal modulation is low. Therefore the distortions of the phase $\Phi(\delta)$ are also low in such a case and Eqn (4) is close to a linear one.

As the values of the factors $r_1$ and $r_2$ are increased variations of the constant component, the amplitude and the distortions of the phase $\Phi(\delta)$ are badly augmented. The depth of modulation of the signal obtained from photoelectric conversion of the reflected interfered light decreases, while that of the signal resulting from photoelectric conversion of the transmitted interfered light increases. Thus, the nonlinearity of Eqn (4) increases, too.

In order to determine an optical length $\delta$ of light path within a preset interval, according to the invention, one must measure the phase $\phi$ of the resultant electric signals and find the desired value of $\delta$ by solving Eqn (4) $\delta = \delta(\phi)$.

One should take notice of the fact that when separated from the original light beam are the beams with circular polarizations $\alpha°$ and $\beta°$ featuring opposite directions of rotation of the electric field vector, the interfering beams of the reflected light will have circular polarizations $\alpha°$ and $\beta°$, whereby the light of the mixed reflected beams is to be split into the components $\epsilon_\alpha°$ and $\epsilon_\beta°$ having circular polarizations, whereas the interfering beams of the transmitted light will have linear polarizations $\alpha'$ and $\beta'$, so that the light of the mixed transmitted beams is to be split into the components $\epsilon_\alpha'$ and $\epsilon_\beta'$ having linear polarizations. Neither the shape of electric signals obtained nor the sequence of operations will be affected.

Another practicable embodiment of the proposed method consists in that, according to the invention, the value of the phase $\phi_* = 2\delta_*$ is preset, to which corresponds a known value of an optical length $\delta_*$ of light path.

Then the optical length $\delta$ of the light path interval is changed, e.g., by displacing one of the reflecting surfaces, or by varying the refractive index on a known section of the preset interval, whereupon the value by which the optical length of the light path interval has changed is measured.

Simultaneously one must measure the phase $\phi$ of the resultant electric signal and than compare the measured value to the preset value of the phase $\phi_*$.

Once the measured values of $\phi$ and $\phi_*$ have become equal, the respective value of $\Delta\delta$ is registered by which the light path optical length has changed.

To find the desired value of an optical length $\delta$ of light path one must subtract the registered value of $\Delta\delta$ by which the interval optical length has changed, from the known value of $\delta_*$ of the light path optical length $$\delta = \delta_* - \Delta\delta = \tfrac{1}{2}\phi_* - \Delta\delta. \qquad (5)$$

The aforedescribed embodiment of the proposed method can be applied for automatic adjustment of a preset optical length $\delta$ of light path interval. In such a case the value of U can serve as an error signal, being proportional to a difference between the phases under comparison $U \sim \phi - \phi_*$.

It stems from Eqn (4) that an average change of the phase $\phi$ of electric signals by the value of $2\pi$ will correspond to a change in the optical length $\delta$ by the value of $\rho$. This implies that an average sensitivity $(\partial\phi/\partial\delta)_{av}$ of the present method equals 2.

However, nonlinearity of Eqn (4) results in that the sensitivity $(\partial\phi/\partial\delta)_m$ in the vicinity of the value of $\delta_m$ of the desired optical length of the light path interval, which values are equal to $$\delta_m = \pi/4(2m-1), \qquad (6)$$

where m is an integer, can be many times the average value of $(\partial\phi/\partial\delta)_{av}$. For instance, when $r_1^2 = 0.4$ and $r_2^2 = 1$, the sensitivity of measuring the light path optical length in the neighbourhood of points is two times the average sensitivity, i.e., $$(\partial\phi/\partial\delta)_m \approx 2(\partial\phi/\partial\delta)_{av} \approx 4.$$

The above-stated specific feature can be utilized for attaining higher accuracy of measurement of the light path optical length $\delta$, whenever in the second embodiment of the present method the value of the phase $\phi$ of an electric signal is preliminarily measured and the value of the phase $\phi_*$ is preset to be equal to one of the values of $\phi_m = 2\delta_m = \pi/2(2m-1)$ nearest to the previously measured value of $\phi$.

A known value $\delta_m$ of the light path optical length corresponds to a preset value of $\phi_* = \phi_m$.

The desired value of optical length $\delta$ of light path is determined by subtracting the thus-found value of $\Delta\delta$ of alteration of the light path interval optical length from the known value of $\delta_m$ in pursuance of Eqn (5).

However, inconstancy of the values of A ($\delta$) and B ($\delta$), as well as nonlinearity of Eqn (4) might be the source of errors of measurement of the light path optical length, especially in the cases where the reflecting surfaces feature high luminous reflectance values.

Figure 2A:
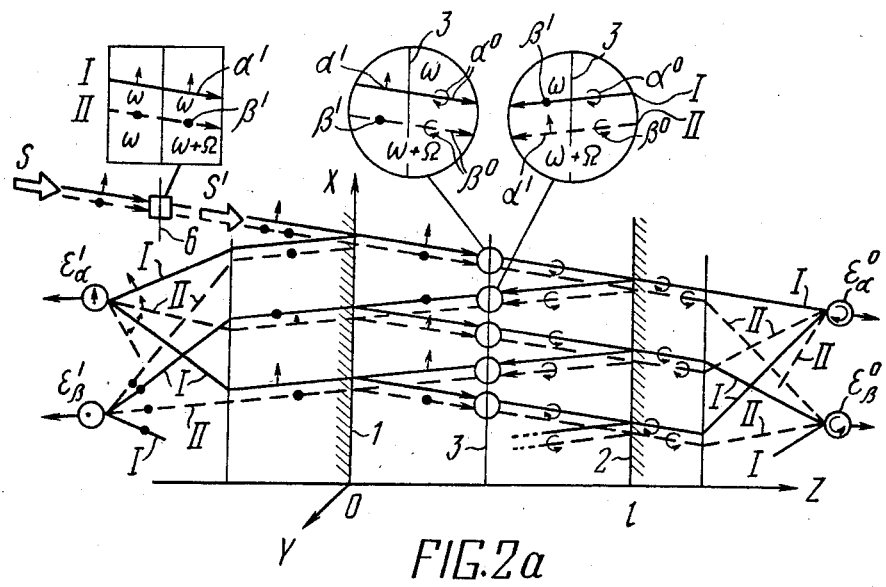
FIG. 2A is a schematic view of a path of light rays when forming the interfering light beams within a preset light path interval and conversion of light polarizations, according to the method for measuring an optical length of light path of the invention.
Figure 2B:
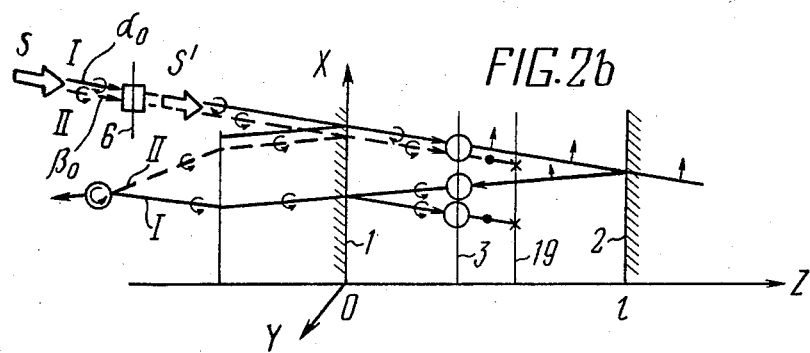
FIG. 2B is the view of FIG. 2A in the case of suppression of the light of one of the independent polarizations when forming the interfering light beams, according to the invention.

This, however, is not the case when, according to the invention, mutual conversion of the polarizations of the light components I and II within a preset light path interval is followed by suppressing the light having one of the polarizations (FIG. 2B). Assume that the components I and II of the original light beam S' have circular polarizations $\alpha°$ and $\beta°$. A first reflected interfering light beam has the both light components with invariable polarizations $\alpha°$ and $\beta°$. The light components that have passed through the reflecting surface of the reflecting element 1, acquire linear mutually square polarizations past the section, wherein the birefringent plate 3 is situated, that is, the light having an original polarization $\alpha°$ assumes polarization $\alpha'$, while the light having an original polarization $\beta°$ assumes polarization $\beta'$. Here, the light component having either of the linear polarizations, e.g., $\alpha'$ is suppressed so that only the light component having polarization $\beta'$ is incident alone upon the surface of the reflecting element 2. Part of the light is transmitted through the surface of the reflecting element 2, while the other part thereof is reflected from this surface and, while on the return run, undergoes, in the section of the birefringent plate 3, conversion of the linear polarization $\beta'$ into the circular polarization $\alpha°$, which has an opposite direction of rotation of the electric field vector with reference to the original circular polarization $\beta°$ of said component. Part of the light of this component is transmitted through the surface of the reflecting element 1 to form a second interfering light beam. The remaining part of the light component in question on its path from the surface of the reflecting element 1 to the surface of the reflecting element 2 undergoes conversion of the polarization $\alpha°$ into the linear polarization $\alpha'$ square with the linear polarization $\beta'$ of this light component, said linear polarization $\alpha'$ having occurred during the first run of light beam from the surface of the reflecting element 1 to the surface of the reflecting element 2. The remaining light of the component under consideration, having the polarization $\alpha'$, is suppressed. Thus, there exists only the beam of the transmitted light alone, whereby no interference pattern arises.

The two thus-formed beams of the reflected light are mixed together, whereupon the light beam is split into two beams having different circular polarizations. Thus, only one light component is present in one of the light beams; that is why no interference pattern occurs therein, whereas double-beam interference arises in the other light beam.

The constant component and the amplitude of the variable component of the electric signal resulting from double-beam inteference are independent of the light path optical length $\delta$ within a preset interval and are not therefore the sources of errors. Relationship between the desired value of $\delta$ and the electric signal phase $\phi$ is expressed by the following simple linear relation.

$$\phi = 2\delta. \quad (7)$$

To solve this relation is also quite simple:

$$\delta(\phi) = \phi/2$$

In such a case no increase in the sensitivity occurs, but the linear relation $\phi = 2\delta$ ensures equally accurate measurement throughout the entire range of change of the light path optical length $\delta$ in a preset interval.

When the light path optical length $\delta$ being measured varies with time, i.e., $\delta = \delta(t)$, the phase $\phi(t)$ of the resultant electric signals varies accordingly. Thus, changes in the light path optical length can be studied in real time by measuring and recording continuously the variations of the value of $\phi(t)$ as a function of time.

In a great many cases of interest is the examination of an interference pattern as a bivariate distribution of the light path optical length $\delta(\rho) = \delta(x,y)$ in the plane of coordinates OXY in a cross-section of the interfering light beams. In such cases photoelectric conversion of the interfered light is carried out at many points $\rho = (x,y)$ of the interference pattern, the values of the phases $\phi(\rho) = \phi(x,y)$ of electric signals obtained at every point of the interference pattern are measured, and the desired distribution of the light path optical length $\delta(x,y)$ in a cross-section of the interfering light beams is found by the distribution of the values of the phases $\phi(x,y)$ in the aforesaid section.

In in such a case there are measured the differences between the phases of pairs of signals corresponding to the pairs of points in the beam cross-section selected along the directions of interest on the interference pattern, so the values of the gradients of the light path optical length along these directions are obtained.

It should be pointed out that the phase value of a signal in the sense implied hereinbefore, consists in a general case of a whole number F of the cycles of $2\pi$ and a fractional part f of such a cycle within 0 and $2\pi$ $$\phi = 2\pi(F+f) \quad (8)$$

Having substituted expressions (2) and (8) to Eqn (4) or (7) and taking into account the periodicity of the value of $\Phi(\delta)$, one obtains the following relation:

$$F = 2D,$$

as well as the following expression for the desired light path optical length $\delta$:

$$\delta = 2\pi d(f) + \pi F, \quad (9)$$

where d(f) is in effect the solution of Eqn (4) or (7) with $f = \phi$ and $d = \delta$.

When measuring the phase of an electric signal only the fractional part f is determined unambiguously, whereas the integral number F of the phase cycles remains undetermined.

Such phase measurement procedures enable one to measure only variations of the light path optical length $\Delta\delta = \Delta a$ with time or over the interference pattern field. To this end the time intervals between the readings and the distances between the measurement points are so selected that the signal phases measured would differ by less than $2\pi$, and the number of the phase cycles F is counted in the forward or reverse direction depending upon the sign of reversal of the phase $\phi$.

To determine the whole number F of the signal phase cycles, the present invention proposes that the fractional part $f\lambda$ of the signal phase be measured additionally with different wavelengths $\lambda$ of coherent light. The number p of additional measurement procedures and the values of an additional wavelength $\lambda$ depend upon the measurement range $\delta_{max}$ of the light path optical length and upon the error of measuring the fractional part f of the signal phase cycle.

The method for measuring a complete optical length of a light path interval, according to the invention, consists of the following steps:

A beam of coherent light is built up, having a known wavelength $\lambda_o$; the fractional part $f_o$ of the phase is measured.

The number p of coherent light beams are created either simultaneously or consecutively, having wavelengths $\lambda_1, \lambda_2, \lambda_3 \ldots \lambda_j \ldots \lambda_p$, obeying the following equations:

$$\lambda_j = \frac{\lambda_o}{1 - H^{p+1-j}}; \quad (10)$$

where
P = int $[1 + \ln(\delta_{max}/2\pi)/\ln(1/\mathcal{X})]$, (int [a] being an integral part of the number a), depends upon the range $\delta_{max}$ of measurement of the light path optical length;

$\mathcal{X} < 1$ is the value depending upon the error of measuring the fractional part f of the cycle.

A corresponding value of $f_j$ of the phase cycle fractional part is measured for each wavelength $\lambda_j$;

The value of $\Delta f_j$ is found from the following formula:

$$\Delta f_j = f_o - f_j + \tfrac{1}{2}\left(1 - \frac{f_o - f_j}{\text{abs}(f_o - f_j)}\right);$$

The value of $F_j$ is determined by the following formula:

$$F_j = \text{int}\left(\frac{\Delta f_{j-1}}{\mathcal{X}} - \Delta f_j + \tfrac{1}{2}\right) \quad (11)$$

A full number $F = F_{p+1}$ of the phase cycles is determined by Eqn (11), where $\Delta f_{p+1} = f_o$;

The desired value of $\delta$ of a preset interval of light path is searched out, using Eqn (9):

$$\delta = 2\pi d(f_o) + \pi F_{p+1}.$$

The laser interferometer as proposed in the invention to carry into effect the method for measuring the optical length of a preset light path interval incorporates the following components (FIG. 4):

a laser 4 capable of emitting a coherent light beam S having a known wavelength $\lambda_o$;

a device 5 situated past the laser 4 as along the direction of run of the coherent light beam and adapted for separating two collinear light components I and II featuring independent polarizations $\alpha$ and $\beta$;

a device 6 for offsetting the light frequency of one of said components with respect to that of the other component by a value of $\Omega$, said device being located past the laser 4 as along the run of the coherent light beam S and being functionally associated with the device 5;

a master oscillator 7 of a radio-frequency electric signal, connected to the light frequency offsetting device 6;

two reflecting elements 1 and 2 arranged successively against each other as along the run of the light beam on a preset light path interval and adapted for forming a number of interfering light beams by multiple reflecting of the light therebetween;

a birefringent plate 3 placed in between the reflecting elements 1 and 2 and adapted for mutual conversion of the polarizations $\alpha$ and $\beta$ of said light components I and II;

a photorecorder 8, comprising a quadratic photoelectric converter 9 such as, e.g., a photocell or photomultiplier tube, and a radio-frequency electric signal phase measuring unit 10 connected to the output of the photoelectric converter 9;

a polarizing element 11 positioned before the photorecorder 8 and adapted for separating part of the interfered light having either of the polarizations $\alpha$ and $\beta$ and directing it to the photorecorder;

a computer device 12 connected to the output of the phase measuring unit 10.

The interferometer under consideration operates as follows. The coherent light beam S emitted by the laser 4 is admitted to pass to the device 5, which separates from the beam S two components I and II having different independent polarizations $\alpha$ and $\beta$, either linear mutually square or circular ones, and featuring opposite directions of rotation of the light electric field vector. The device 6 shifts the light frequency of one of the aforesaid components, e.g., the component II, by the value of $\Omega$ falling within the radio-frequency range. The device 5 splits the components I and II spatially into separate beams, which are brought in coincidence again both in cross section and in the direction of propagation after the frequency has been offset. It is important that past the devices 5 and 6 a light beam S' be formed with the two collinear components I and II having independent polarizations $\alpha$ and $\beta$, and different frequencies $\omega$ and $\omega+\Omega$. The aforesaid light beam S' undergoes multiple-beam interference when repeatedly reflected from the elements 1 and 2, whereby according to theory, the beating of the intensity of the transmitted and reflected interfered light arises with each polarization, having a frequency $\Omega$ and a phase $\phi$, which is interrelated with the desired value of $\epsilon$ through Eqn (4).

The photoelectric converter 9 converts the beating of the light intensity into a radio-frequency electric signal having a frequency $\Omega$ and a phase $\phi$, while the unit 10 measures its phase. The computer device 12 finds the solution of Eqn (4), which is the desired optical length $\delta$ of a preset light path interval between the reflecting elements 1 and 2.

The device 5 can be so implemented as to separate the light components I and II featuring circular oppositely directed polarizations $\alpha°$ and $\beta°$, which is the case when used as the devices 4, 5 and 6 in the proposed interferometer is a dual-frequency laser utilizing the Zeeman effect for separating the light components I and II and shifting the light frequency of one of the separated components. In such a case the light components I and II of the interfering light that has passed through the reflecting elements 1 and 2 feature linear mutually square polarizations $\alpha'$ and $\beta'$. The polarizing element 11 splits the beam of the interfered light into two beams having the aforesaid linear polarizations $\alpha'$ and $\beta'$.

When the device 5 is so made as to separate the light components I and II having linear mutually square polarizations $\alpha'$ and $\beta'$, e.g., as a double-beam polarization interferometer as described in a paper by N. A. Massie published in the journal "Applied Optics", vol. 19, No. 1, 1980, pp. 154 through 160, the components of the interfering beams of light that has passed through the reflecting elements 1 and 2, feature circular polarizations $\alpha°$ and $\beta°$. In such an embodiment of the laser interferometer a quarter-wave plate 13 (FIG. 5) should be placed before the polarizing element 11, capable of converting circular polarizations into mutually square linear ones.

It ensues from the method described hereinbefore that with the high values of the factors $\tau_1$ and $\tau_2$ of light transmission through the reflecting elements 1 and 2, the beating of the interfered light intensity features but low depth of modulation $Q=V/A$, which results in a low ratio of the radio-frequency electric signal to shot noise and hence in a high error of measuring the signal phase $\phi$. On the other hand, with the low values of the factors $\tau_1$ and $\tau_2$ of light transmission through the elements 1 and 2 there is observed bad nonlinearity of the relationship between the electric signal phase $\phi$ and the desired optical length $\delta$ of the light path interval as represented by Eqn (4).

A beam-splitter element 14 is provided between the light frequency offsetting device 6 and the reflecting element 1 aimed at registering the interference pattern in a reflected light, said beam-splitter element being to separate the reflected interfering light beams, while the polarizing element 11 and the photorecorder 8 are arranged on an optical axis of the interfering beams separated by the beam-splitter element 14. When the polarization of the components of the original light beam S' are linear, the polarizations of the components of the reflected interfering beams are linear, too. In such a case the interferometer will feature the diagram of FIG. 6.

When the polarizations of the components of the original light beam S' are circular, the components of the reflected interfering beams have circular polarizations as well. In such a case the quarter-wave plate 13 (FIG. 5) should be placed before the polarizing element 11.

Figure 4:
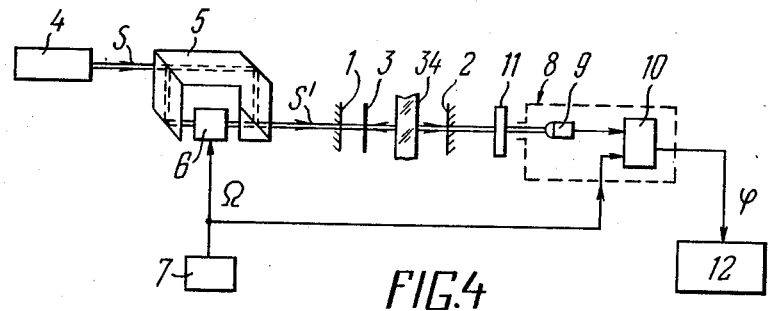
FIG. 4 is a block-diagram of one of the practicable embodiments of a laser interferometer using interference of transmitted light rays, according to invention.
Figure 5:
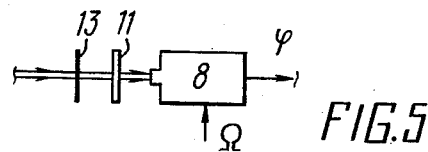
FIG. 5 illustrates an embodiment of the recording portion of the interferometer of FIG. 4 in the case where use is made of circular polarizations of the separated light components in an original light beam, according to the invention.
Figure 6:
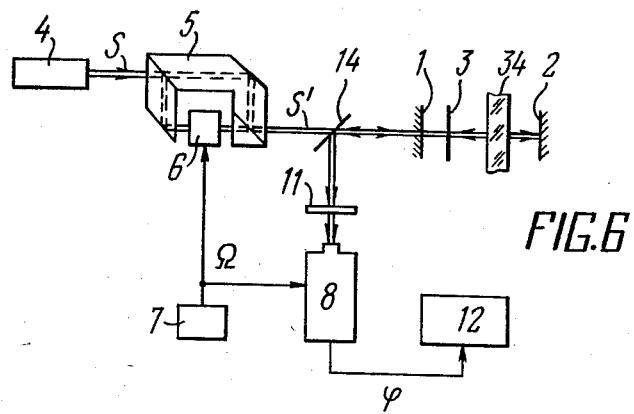
FIG. 6 is a block-diagram of one of the practicable embodiments of the laser interferometer using interference of reflected light rays, according to the invention.

In one of the embodiments the aforesaid polarizing element 11 is in fact a polarizer, which transmits to the photorecorder the interfered light featuring one of the independent linear polarizations $\alpha'$ and $\beta'$ and suppresses the light having the other of the aforesaid polarizations (FIGS. 4 to 6).

Figure 7:
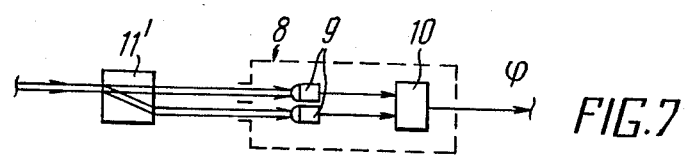
FIG. 7 is a schematic view of an embodiment of the recording portion of the laser interferometer when a polarization beamsplitter is used as the polarizing element, according to the invention.

The polarizing element 11 can also be made as a polarization beam-splitter 11', e.g., the Glan or Wollaston prism, etc. capable of dividing the interfered light beam into two beams featuring linear mutually square polarizations $\alpha'$ and $\beta'$, while the photorecorder is fashioned as the two photoelectric converters 9, of which one is arranged on the optical axis of one of the separated beams, and the other converter, on the optical axis of the other beam (FIG. 7). It follows from Eqns (3) and (3') that the radio-frequency electric signals resulting from photoelectric conversion of the interfered light in said separated beams are similar to each other, but have their phases $\phi$ of the opposite signs. Both of the photoelectric converters 9 and 9' are connected to the same phase measuring unit 10, one of them to the measuring input and the other to the reference input thereof. In such a case the phase measured value is twice the phase $\phi$ value in each signal. With such an embodiment of the polarizing element and the photorecorder the laser interferometer has doubled sensitivity as compared to the aforedescribed embodiments of the laser interferometer.

It has been known that higher sensitivity of an interferometer can be obtained using nonlinearity of Eqn (4). Such an interferometer (its diagram being represented in FIG. 8) comprises:

a device 15 for changing an optical length $\delta$ of a preset light path interval with a transducer 16 capable of registering the value $\Delta\delta$ of such changes;

a unit 17 for presetting the phase values $\phi*$ corresponding to known values $\phi*$ the light path interval optical length, connected to the output of the phase measuring unit 10;

a unit 18 for comparing the measured and preset phase values, the inputs of which are connected respectively to the units 10 and 17. The computer device 12 is connected to the transducer 16 and the unit 17.

The laser interferometer of the aforedescribed embodiment operates as follows. In the initial position the device 15 assumes the neutral position, wherein the light path interval is of the desired optical length. The unit 10 measures the electric signal phase $\phi$ corresponding to the optical length $\delta$ of a preset interval. The value of the phase $\phi$ is impressed upon the unit 17, which assigns the value of the phase $\phi* = \phi_m$ nearest to the value of $\phi$, to which corresponds, according to Eqn (6), a known value $\delta* = \delta_m$ of the interval optical length. The measured value of the phase $\phi$ and the preset value of the phase $\phi*$ arrive at the input of the phase comparator unit 18, wherein the values of the $\phi$ and $\phi*$ are compared and an error signal u is produced, which is proportional to a difference between the phase values being compared, $u \sim \phi - \phi*$. Being actuated by the error signal u the device 15 changes the optical length of the interval. At the same time the value of the phase $\phi$ of the radio-frequency electric signal at the output of the unit 10 and the magnitude of the error signal u are changed as well. The length of the light path interval is changed until the value of the phase $\phi$ at the output of the unit 10 gets equal to the preset value of the phase $\phi*$, and the error signal u becomes equal to zero. In response to the zero error signal from the comparator unit 18 the computer device 12 subtracts the value $\Delta\delta$ of a change in the interval optical length as registered by the transducer 16, from the known value of $\delta*$ corresponding to a preset value of the phase $\phi*$.

Figure 9:
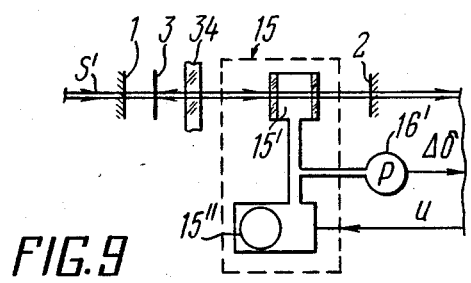
FIG. 9 illustrates an embodiment of the device for changing the light path interval optical length, which is in fact a pressure-tight cell filled with a gas under a known pressure, according to the invention.

The device 15 for changing the optical length of a ligth path interval can be made as a pressure-tight cell 15' having a known length, placed in between the reflecting elements 1 and 2 and filled with a certain gas, and a compressor 15" adapted for changing the pressure P of said gas in the cell at a constant temperature. The transducer 16 for registering a change in the light path optical length can be made in such a case as a gas pressure transducer 16' (FIG. 9).

Figure 10:
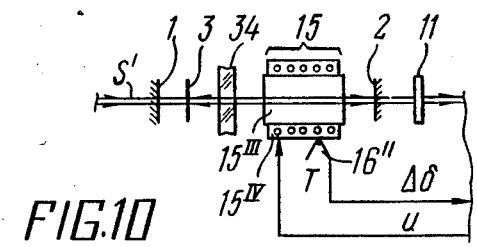
FIG. 10 illustrates an embodiment of the device for changing the light path interval optical length, which is essentially an element made from a known material and having a known temperature, according to the invention.

The device 15 can also be made as a known-length cell 15''' of a known material and a heater element 15'''', both being positioned between the reflecting elements 1 and 2. Such being the case the transducer 16 may be made as a sensor 16" of temperature T (FIG. 10).

Figure 8:
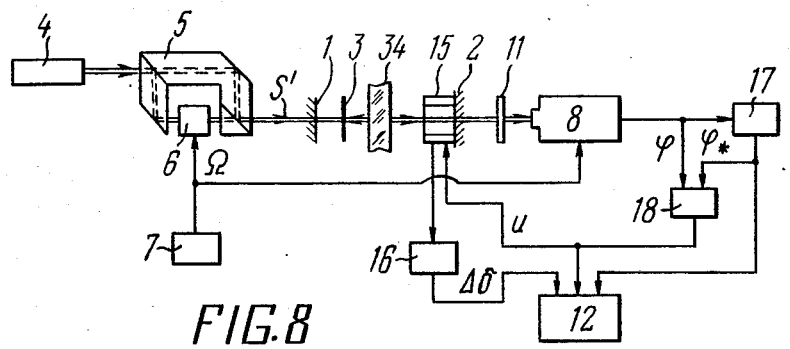
FIG. 8 is a schematic view of one of the practicable embodiments of the laser interferometer featuring higher sensitivity and a possibility of automatic adjustment of the light path interval optical length, according to the invention.
Figure 11:
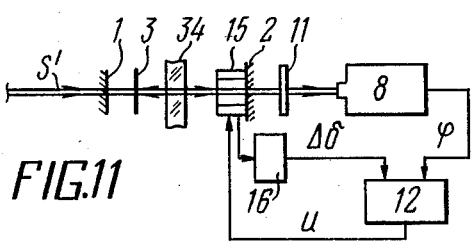
FIG. 11 illustrates an embodiment of the phase presetting unit and the phase comparator unit, which are in fact a computer, according to the invention.

The units 17 and 18 can be implemented as self-contained digital or analog electronic computing devices as shown in FIG. 8. However, their functions can be performed directly by the device 12 which is in fact a computer. The diagram of such an interferometer is shown in FIG. 11.

The interferometer described hereinbefore can be successfully applied for stabilizing a preset optical length of the light path interval between the reflecting elements 1 and 2.

When measuring the optical length of a preset interval using a laser interfrometer featuring non-linear relation as to Eqn (4), the various values of $\delta$ will be measured with different degrees of accuracy. To provide linear relationship as to Eqn (7), according to the invention, the laser interferometer comprises a polarizer 19 placed between the reflecting elements 1 and 2 past the birefringent plate 3 (FIG. 12). To obtain proper operation from the interferometer of such an embodiment the device 5, when forming the original light beam, should separate circular polarizations having the electric field vector rotating in the opposite directions. The first inteferring light beam is formed upon the light is reflected from the reflecting element 1. When the light runs within the preset path interval from the reflecting element 1 towards the element 2 the circular polarizations of the original light beam components are converted into the linear mutually square polarizations, and one of the light components is suppressed by the polarizer 19. The other component returns to the reflecting element 1 after having undergone the conversion of the linear polarization of the aforesaid component in the plate 3. Part of the light of said component is transmitted through the reflecting element 1 to form another interfering light beam. The remaining part of the light of the second component is suppressed during a second pass of the light from the element 1 to the element 2. The reflected first and second beams are mixed together to form two-beam interference. The phase $\phi$ of the interfered light intensity beating depends linearly upon the optical length $\delta$ of a light path interval and is determined by Eqn (7).

The reflecting elements 1 and 2 adapted for assigning a light path interval and forming the interfering light beams, in a simplest case as has been considered hereinbefore (refer to FIGS. 4, 6, 8), can be spaced a preset distance apart and against each other on the same optical axis OZ of the original light beam S'. The interfering light beams are formed upon multiple light reflection within an interval between the mirror surfaces of the reflecting elements 1 and 2. The best interferometer performance is obtainable when the birefringent plate is in fact a quarter-wave plate. In particular, the reflecting elements 1 and 2 may be in fact partially reflecting mirror surfaces, either flat or shaped more intricately.

At least one of the reflecting elements 1 and 2 may be in effect a diffraction grating 1' or 2' so positioned that the axis of the light beam of one of the orders diffracted by said grating should align with the axis on which the reflecting elements are arranged. The original light beam S' can be admitted into the space between the gratings 1' and 2' or through one of these gratings, which is the case with the mirror surfaces (FIGS. 4, 6), or also at a diffraction angle to the diffraction grating 1' (FIG. 13A). The photorecorder 8 can also be arranged either on the beam axis as in the case of the mirror surfaces (FIGS. 4 and 6) or on the axis of one of the beams from the diffraction grating 2' (FIG. 13B). The interferometer operates in this case in a way similar to that described before.

The reflecting elements 1, 2 and 2", three or more in number, can be placed at the corners of a closed polygon representing a preset light path interval (FIG. 14). The original light beam passes through the partially reflecting element 1 and then performs multiple runs along the closed polygon in the same direction, being consecutively reflected from the elements 2, 2" and 1. On each pass the light acquires an additional offset of the light wave phase equal to the optical length $\delta$ of the closed polygon and conversion of polarization by the birefringent plate 3. In addition part of the light is separated by the element 1 during each run thereof to emerge from the closed polygon and form a next interfering beam. The photorecorder 8 is arranged on the axis of the interfering beams emerging from the closed polygon. The best interferometer performance is obtained in this case when the birefringent plate is in fact a half-wave plate.

The diffraction grating 1' or 2' used as the reflecting element 1 and 2 in the aforementioned pattern of the preset light path interval, is so positioned that the light beam reflected in one of the diffraction orders, e.g., in the first, gets incident upon the next (third) reflecting element 2" (FIG. 15) as along the run of the light beam within a preset light path interval.

Figure 15:
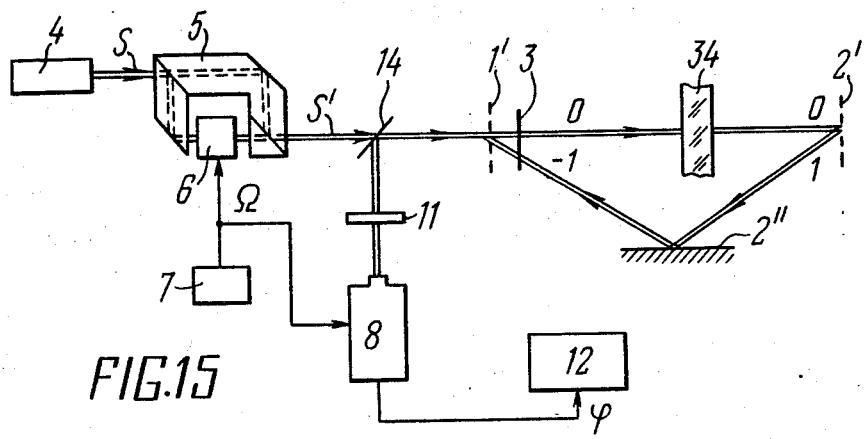

Now let us consider the operation of the interferometer whose schematic diagram is illustrated in FIG. 15. Used as the first reflecting element 1 is the partially transparent diffraction grating 1'. Located oppositely to the grating 1' is the second reflecting element in the form of the reflecting diffraction grating 2', while the third reflecting element may be a mirror surface.

The original light beam S' is transmitted through the fully transparent diffraction grating 1', thus becoming dispersed into a number of diffracted beams. The zero-order beam is incident upon the reflecting grating 2' to be dispersed again into a number of orders. The beam of the first diffraction order from the grating 2' gets onto the third reflecting element 2" and is reflected therefrom to become incident upon the diffraction grating 1' at an angle of the minus-first order diffraction. Upon interacting with the grating 1' the beam is separated again into a number of the diffracted beams, some of which come out of the preset interval via the grating 1' outwards, while the other beams are reflected. The beam of the minus-first order reflected from the grating 1 follows the path of the original zero-order beam, and its path is reiterated many times.

The birefringent plate 3 is in fact a half-wave plate when the beams of only one diffraction order pass therethrough, or a plate featuring a quarter-wave difference between the light wave phase shifts in the two working orders, which is the case when the plate 3 is placed close to one of the diffraction gratings.

Multiple-beam interference occurs in each of the diffracted beams of the light that has emerged from the interval through the grating 1', which is described by the theory of the proposed method. That is why the photorecorder 8 of a multiple-beam interference pattern can be placed across the path of any one or several diffracted beams.

Such a construction pattern of a preset light path interval can be used whenever it is necessary to measure the light path optical length on a curved interval, or pass the light beam within a preset interval in one direction only.

Used as the aforesaid diffraction gratings 1' and 2' can be, e.g., holograms.

In a majority of problems solved with the help of interferometry it is necessary to measure the shape or distortion of the light wavefront, which has passed over a preset path interval, i.e., to measure the optical lengths of a preset interval along the run of the rays passing through preset points $\rho=(x,y)$ of the cross-section of the interfering light beams.

Such a problem can be solved with the help of the proposed laser interferometer for which purpose it incorporates, according to the invention, an optical system 20 placed before the reflecting elements (FIG. 16) and adapted for expanding the original light beam S'.

Figure 16:
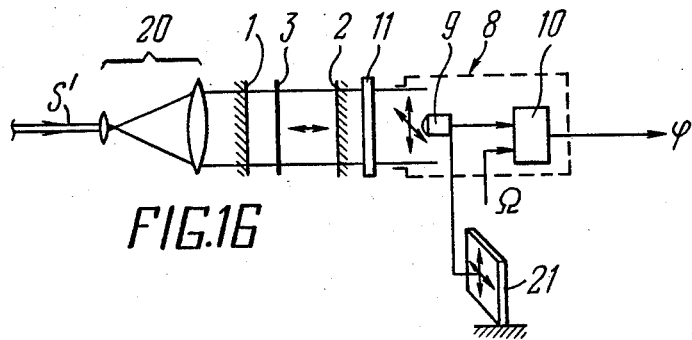

In such a case the photorecorder 8' should be capable of converting the intensity of the interfered light at different points across the interfering light beams. To this end the photoelectric converter 9 is provided with a device 21 adapted for scanning an interference pattern (FIG. 16). The scanning device 21 may be made as a mechanical contrivance for moving the photoelectric converter through the points of an interference pattern, or as an electro-optic or acousto-optic deflector, an image dissector, etc.

It should be noted that a signal produced by the master oscillator 7 serves as a reference signal for measuring the phase of an electric signal. In this case the device 5 for separating the light components of the original beam S' and the device 6 for offsetting the light frequency of one of said components may introduce on error into the results of measuring the phase $\phi$. An average value of these phase disturbances is eliminated during the initial calibration; however, random phase disturbances during the scanning of an interference pattern lead to errors in measuring the distribution of the light path optical length.

Figure 17:
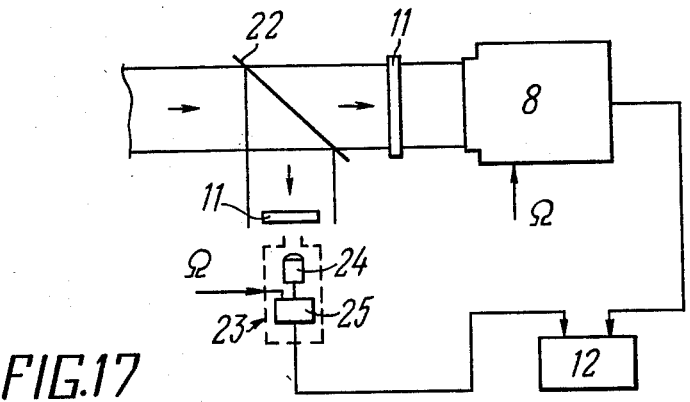

To obviate such errors the laser comprises an optical beam-splitter element 22 provided before the photorecorder 8 and adapted for separating part of the interfered light and directing it onto an additional photorecorder 23, comprising an additional photoelectric converter 24 and an additional phase measuring unit 25 (FIG. 17). The electric signal of the additional photoelectric converter 24 can be used as a reference signal for measuring the phase by the unit 10 of the main photorecorder. Phase distortions can also be eliminated by subtracting the results of phase measurement by the additional photorecorder from those by the main photorecorder, using the computer device 12, if the same signal has been used as a reference signal for the units 10 and 25 in measuring the aforesaid phases, e.g., the signal of the master oscillator 7.

Both the main and additional photoelectric converters 9 and 24, respectively, may be made as a photoelectric quadratic detector 9' and 24', e.g., a photomultiplier tube or photodiode adapted for converting the interfered light at a number of points on the interference pattern one-by-one as the scanning occurs.

Figure 18:
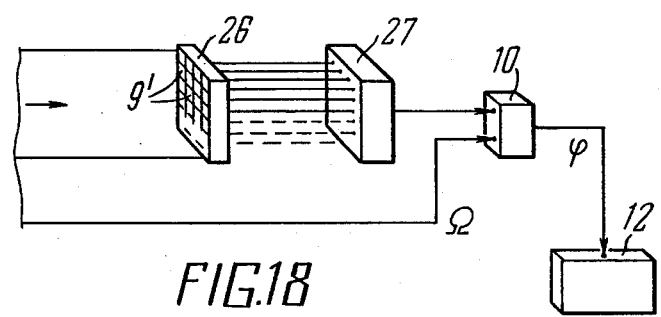

The main photoelectric converter 9 and the additional photoconverter 24 may also be made as a photodetector array 26 or 26', consisting of a number of the photodetectors 9' or 24', the outputs of every photodetector being connected to the phase measuring unit 10 or 25 through a switching device 27 of electric signals. Apart from the aforedescribed scanning means, the scanning of an interference pattern can be effected by the switching device 27 of the main photorecorder by switching the output signals of the quadratic photodetectors 9' (FIG 18).

Such an interferometer is suitable for measuring the optical length of a light path interval either statically or under stationary changes of said interval.

Figure 19:
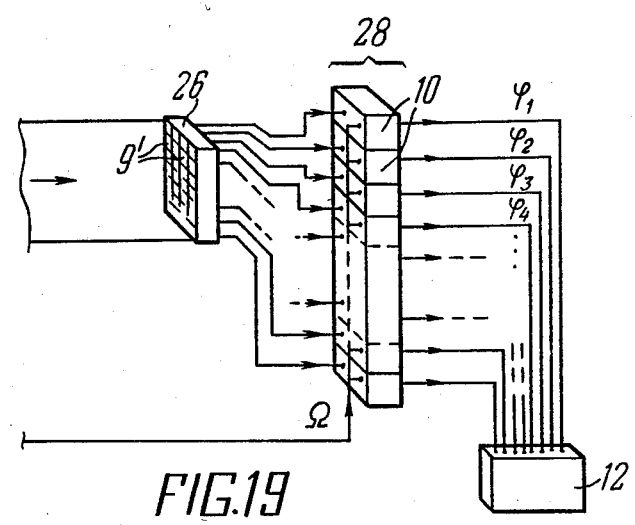
Figure 20:
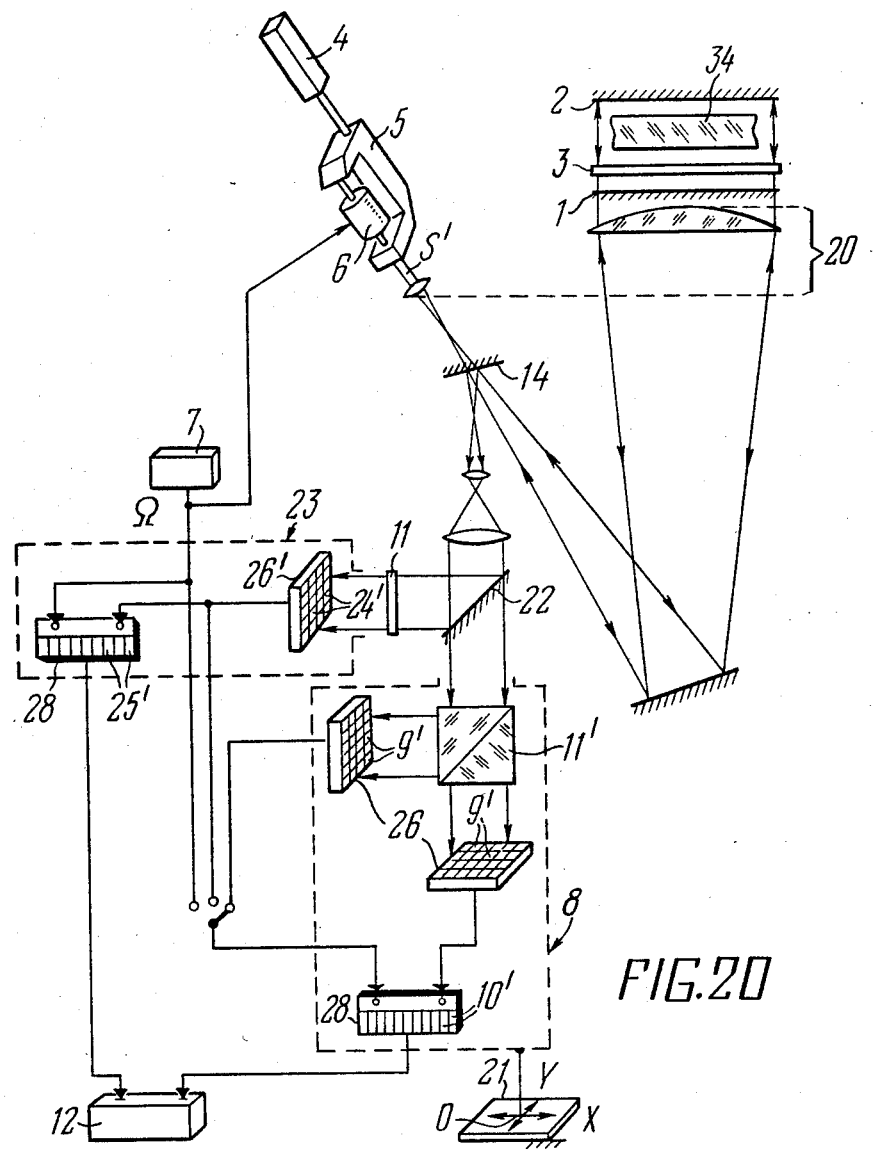

Whenever the optical length of an interval is to be measured under nonstationary changes thereof the output of each of the quadratic photodetectors 9' of the array 26 is connected to its own main phase measuring unit 10' (FIG. 19), while the output of each of the quadratic photodetectors 24' of the additional array 26' can be connected to the own additional phase measuring unit 25' (FIG. 20).

A multichannel phase-metering system 28 is adapted to simultaneously measure the phases of signals, which correspond to a series of points on an interference pattern. The phase values can be registered simultaneously in response to an external locking signal from a timer, the computer device 12, or from any other source. These phase values are then entered into the computer device 12 to represent an instantaneous distribution pattern of the light interval optical length over the cross-section of the interfering beams.

The phases can also be measured by the units 10, 10', 25 and 25' with reference of the signal produced by the master oscillator 7. To this end the reference inputs of the aforesaid units should be connected to the output of said master oscillator 7. Besides, the phases of the signals of some of the photodetectors 9' of the main photorecorder 8 are expedient to be measured with reference to one or more signals from the photodetectors 24' of the array 26' of the additional photorecorder 23. With this purpose in view at least one of the quadratic photodetectors 24' of the additional photorecorder 23 is to be connected to at least one phase measuring unit 10' of the main photorecorder 8. The best embodiment of such an interferometer is diagrammatically shown in FIG. 20.

When the interferometer comprises at least one device 15 for changing the optical length of a light path interval, one transducer 16 for sensing a change in the optical length of a light path interval, one phase presetting unit 17 and one phase comparator unit 18 connected to at least one of the photodetectors according to the diagram of FIG. 8 described hereinbefore, an interference pattern can be stabilized at least one point corresponding to the position of the aforesaid photodetector.

When measuring the distribution of the optical length of a light path interval in a cross-section of large-diameter interfering beams with high resolution with respect to the interference pattern field, a small amount of light gets onto the photoelectric converter 9. This results in a low ratio of useful radio-frequency signal to shot noise, which in turn involves a gross error of measurement of the phase $\phi$. In addition the beam emitted by the laser 4 has its intensity profile approximating the Gaussian curve. Therefore the average intensity of the interfered light across the interfering beams varies badly from point to point. The result is that the phase measuring accuracy in the centre of the interference pattern differs heavily from that at the periphery thereof.

Figure 21:
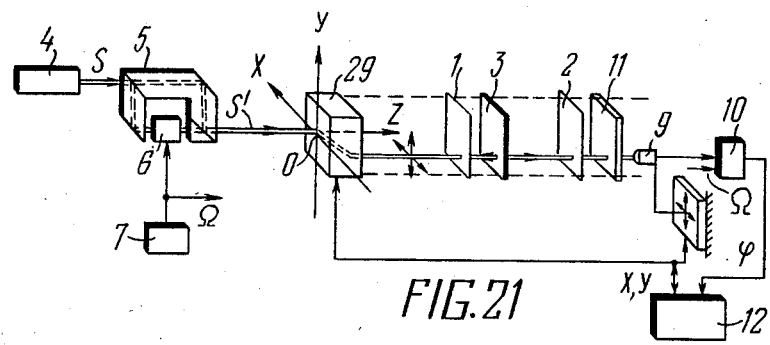

In order to increase the accuracy of measurement of the optical length of a light path interval and to ensure equally accurate measurement over the entire field of an interference pattern, according to the invention, the laser interferometer comprises a device 29 for displacing the original light beam S' parallel to itself in two mutually square directions X and Y perpendicular to the beam axis OZ (FIG. 21). The aforesaid device is situated between the devices 5 and 6 for forming the original light beam, on the one side and the reflecting elements 1 and 2 on the other side. With the collimated light beam S' moving parallel to itself the light wavefront remains all the time parallel to the same plane similar to the wavefront of a wide collimated beam. The distribution of the phases $\phi(\rho)=\phi(x,y)$ of the interfered light intensity beating remains the same as in the case of a fixed wide collimated beam. However, the luminous flux density at the interference pattern points scanned by a pencil beam is several scores or even hundreds of times as high, whereby the signal-to-noise ratio at the output of the photoelectric converter is higher, accordingly.

Figure 22:
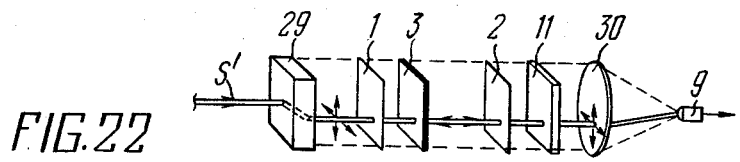

The light of the scanning pencil beam can be directed onto the photoelectric converter by means of, e.g., a converging lens 30 set at a focal length away from the photorecorder (FIG. 22).

The pencil beam of the interfered light can immediately be incident upon the photoelectric converter 9 when the aforesaid device 29 for displacing the light beam parallel to itself will be linked, while moving, with the device 21 for scanning an interference pattern (FIG. 21).

Figure 23:
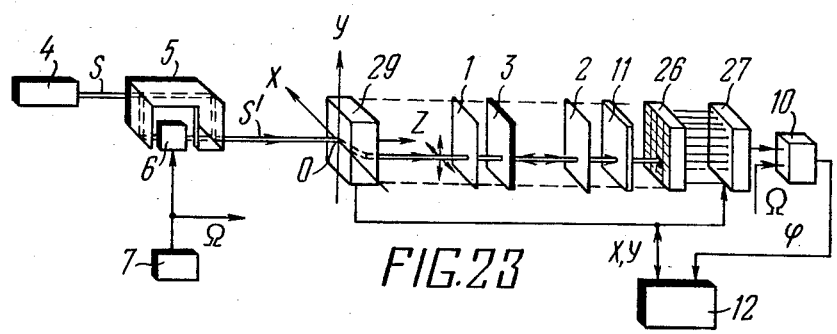

Whenever the photoelectric converter 9 of the photorecorder 8 is essentially the array 26 made up of a number of quadratic photodetectors 9' connected to the phase measuring unit through the switching device 27, the device 29 for the light beam displacement is expedient to be linked with the switching device 27 to provide for their coordinated operation (FIG. 23).

It becomes necessary when tuning the laser interferometer and in the course of measurement, to visually observe the interference pattern or to record its image. However, the light intensity beating occurs at a high frequency, and no interference pattern is observed. To make it possible to record the interferogram image the interferometer comprises a light intensity modulator 31 located before the additional photorecorder 23, and a generator 32 of electric pulses connected to the light intensity modulator 31. In such a case the additional photorecorder 23 is essentially in interferogram image recorder 23' (FIG. 24).

Figure 24:
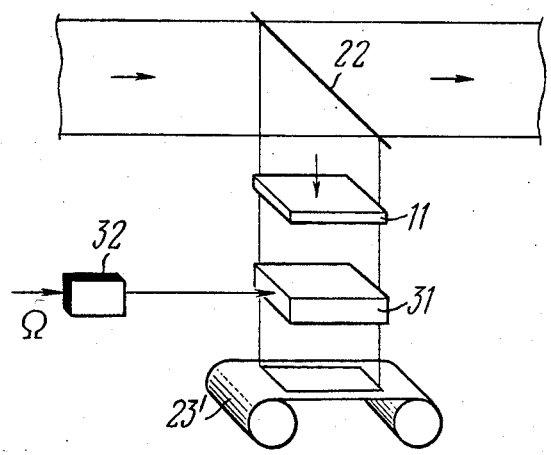

In order that an interference pattern may be observed visually under static conditions the electric pulse generator 32 is connected to the master oscillator 7 and locked with it as to pulse repetition frequency (FIG. 24). An interference pattern, wherein the fringes travel incessantly is projected onto the additional photorecorder 23 only at those instants when the fringes, after having travelled for one spacing, assume the same position. As a result of such gating a fixed interferogram is projected onto the photorecorder, which can be observed visually or with the help of TV appliances, or be photographed, etc. To provide higher stability of the interference pattern observed the electric pulse generator 32 can be connected to either of the photodetectors 9' and 24'.

The phase measuring unit 10 enables one to measure the phase of an electric signal within a full period, that is, the fractional part f of the desired value of the phase $\phi$. All the laser interferometers described before enable one to measure the optical length of a preset light path interval not exceeding one light wavelength in a medium filling the preset interval, as well as changes in the desired optical length within a broad range when continuously looking after the phase changes and counting the number of the phase cycles in the forward or reverse direction depending upon the sign of the phase reversal.

To determine the integral number $D=\mathrm{int}(\delta/2\pi)$ of the wavelengths within the preset interval, which together with the measurement of the fractional part d according to Eqn (2) will give a full value of the optical length of a preset interval within a wide range of $\delta \leq \delta_{max}$ the laser interferometer, according to the invention, comprises the laser 4 featuring retunable wavelength $\lambda$ of the emitted light. The tunability range must provide formation of a coherent light beam with the wavelength values from $\lambda_o$ to $\lambda_p$, and a relative error $\sigma_\lambda/\lambda$ of tuning the wavelength $\lambda_j$ should not exceed the value of $\mathcal{X}/6\, \delta_{max}$. The required laser wavelengths $\lambda_j$ are in this case set in succession and the fractional parts $f_j$ of the phase cycle are measured in succession as well.

Figure 25:
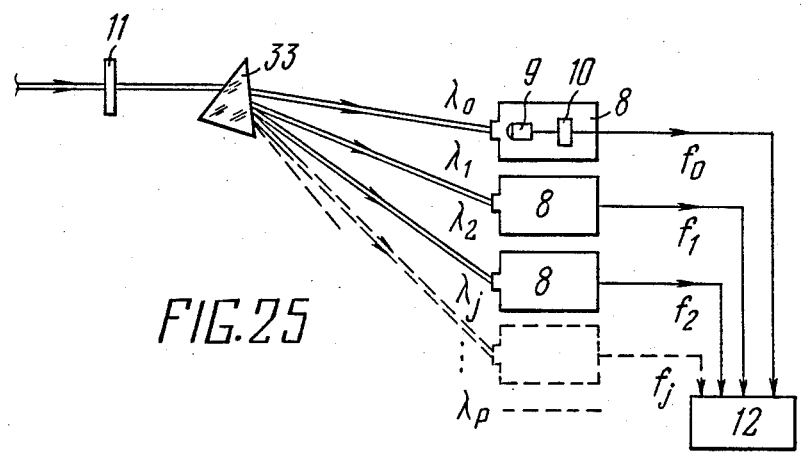

Whenever it is necessary to measure the value of $f_j$ simultaneously on all the wavelengths $\lambda_j$ the laser 4 should be capable of lasing the light of all the mentioned wavelengths $\lambda_o$ to $\lambda_p$ at a time. In addition, such a laser interferometer comprises an optical unit 33 for splitting the interfered light beam into separate light beams depending upon the wavelength values of $\lambda_j$, while the main photorecorder 8 is situated on the optical axis of each of the separated light beams and each of said photorecorders comprises the main photoelectric converter 9 and the phase measuring unit 10 connected to the computer device 12 (FIG. 25). The results of measurement of the fractional parts $f_j$ are inserted into the computer device, wherein there is calculated, in keeping with the method described, the whole number D of the light wavelengths going into a preset light path interval and there is summed up, according to Eqn (2), the number D with the fractional part d calculated also in the computer device 12 from the result of measurement of the fractional part $f_o$ of the phase cycle corresponding to the respective wavelength $\lambda_o$.

The method for measuring the optical length of a preset light path interval as disclosed in this invention enables, for the first time in the trade, the determining of an immediately specified optical length of a preset interval between two reflecting elements in real time and in a digital form. The laster interferometer carrying said method into effect features the most simple and durable construction, is readily tunable and negligibly sensitive to any external action.

The method offers possibilities for providing a new wide class of laser-band multiple-beam digital interferometers operating in real time and capable of high-accuracy and productivity solving of the various problems in measuring distances, displacements and an optical density of transparent media, as well as suitable for being engaged in an automatic control of processes, wherein the optical length of a preset interval may serve as a characteristic parameter.

What is claimed is:

1. A method of measuring an optical length of light path interval, said method comprising:
    building up an original light beam;
    presetting a light path interval;
    forming a number of interfering light beams from said original light beam in such a manner that each next interfering light beams is formed from a preceding interfering light beam by:
        isolating part of the light from the preceding interfering light beam;
        passing the beam of isolated light at least once along said preset light path interval;
        bringing the beam of isolated light out of said light path interval;
        mixing said formed interfering light beams together into a beam of mixed light;
    recording an interference pattern formed in said beam of mixed light;
    building up said original light beam by:
        creating a beam of coherent light;
        separating two colinear components from said beam, including a first light component and a second light component, having two respective independent polarizations;
        offsetting the light frequency of one of said two colinear components with respect to the other;
        converting the polarization of said first light component of the beam of isolated light into the polarization of said second light component, and the polarization of said second light component, into the polarization of said first light component;
    recording an interference pattern formed in said beam of mixed light by:
        dividing said beam of mixed light into two beams of interfered light including a first beam of interfered light and a second beam of interfered light, having said two respective independent polarizations;
        converting said first beam of interfered light having the first of said independent polarizations, into a first electric signal;
        converting said second beam of interfered light having the second of said independent polarizations, into a second electric signal;
        measuring the phase of said first electric signal;
        measuring the phase of said second electric signal;
        determining the desired optical length of said preset light path interval by said phase measured values.

2. A method as claimed in claim 1, wherein the following additional operations are performed for measurement of the optical length of a light path interval:
    presetting at least one phase value corresponding to at least one known value of the light path optical length;
    comparing the phase measured values to one of the preset phase values;
    changing the optical length of said light path interval so as to approximate it to said known value of the light path optical length;
    noting the value of said change in the optical length of said light path interval at the instant when the measured value of the signal phase is equal to the preset phase value;
    subtracting said noted value of change in the optical length of said light path interval from said known value of the light path optical length to determine the desired value of the optical length of a preset light path interval.

3. A method of measuring the optical length of a preset light path interval, said method comprising the following consecutive steps:
    building up an original light beam in the following way:
        creating a beam of coherent light;
        separating two colinear components from said beam, said two colinear components including a first colinear component and a second colinear components, having two respective independent polarizations;
        offsetting the light frequency of one of said components from the other component;
    presetting a light path interval;

forming a first interfering light beam as follows:
  separating a part of the light from said original beam of coherent light which comprises said first coliner component and said second colinear component with independent polarizations and different frequencies;
  bringing the thus-formed first interfering light beam out of said light path interval;
forming a second interfering light beam as follows:
  separating a part of the light from the first interfering light beam;
  passing the part of separated light at least once along said preset light path interval;
  converting the polarization of said first colinear light component in the beam of separated light into the polarization of said second colinear light component while converting the polarization of said second colinear light component into the polarization of said first colinear light component;
  suppressing the component comprising the first of said polarizations suppressing in the beam of separated light;
  bringing the thus-formed second interfering beam of separated light out of said light path interval;
  mixing together said first and second interfering light beams brought out of said light path interval;
  separating a part of the light having the second of said polarizations;
recording an interference pattern formed in the beam of separated light as follows:
  converting the interfered light having the second of said independent polarizations into an electric signal;
  measuring the phase of said electric signal;
  determining the desired optical length of said preset light path interval from the measured phase of said electric signal.

4. A method as claimed in claim 1, wherein for determining temporal variation of the light path optical length within a preset interval, temporal variations of the measured phases of the obtained electric signals are registered, and a change in the optical length of said light path interval is judged by the temporal variation of said measured phases.

5. A method of measuring the distribution of a light path optical length within a preset interval across interfering light beams, said method comprising the following consecutive steps:
  building an original light beam in the following way:
    creating a beam of coherent light;
    separating two colinear components from said beam including a first light component and a second light component, having two independent polarizations, respectively;
    offsetting the light frequency of one of said components from the other of said components;
    presetting a light path interval;
  forming a number of interfering light beams from said original coherent light beam in such a manner that each next interfering light beams is formed from a preceding interfering light beam in the following way:
    separating part of the light beam from the preceding interfering light beam;
    passing the separated part of the light beam at least once along said preset light path interval;
    converting the polarization of said first light component in the beam of a separated light into the polarization of said second light component, and converting the polarization of said second light component into the polarization of said first light component;
    bringing each of said next interfering light beams out of said light path interval;
  mixing together said formed interfering light beams into a single beam of mixed light;
  dividing said beam of interfered light into two beams having said independent polarizations;
  recording an interference pattern in each of said divided beams of interfered light and performing the following operations at no less than two points on the cross-section of the interfering light beams:
    converting the interfered light having the first of said independent polarizations into an electric signal at the first of said points;
    converting the interfered light having the second of said independent polarizations into an electric signal at the first of said points;
    measuring the phases of the electric signals obtained at the first of said points;
    converting the interfered light having the first of said independent polarizations into an electric signal at no less than one other point;
    converting the interfered light having the second of said independent polarizations into an electric signal at no less than one other point;
    measuring the phases of the electric signals obtained at no less than one other point;
    obtaining the distribution of the light path optical length within a preset interval across the interfering light by the results of measurement of the phase of the electric signals obtained at said first and said other points.

6. A method of measuring the optical length of a preset light path interval, said method comprising the following consecutive steps:
  building up an original light beam in the following way:
    creating a beam of coherent light, having a first known wavelength;
    separating two colinear components from said beam including a first light component and a second light component, having two independent polarizations;
    offsetting the light frequency of one of said components with respect to the other light component;
    presetting a light path interval;
  forming a number of interfering light beams from said original coherent light beam in such a manner that each next interfering light beam is formed from a preceding interfering light beam in the following way:
    separating a part of the light from the preceding interfering light beam;
    passing the separated part of light along said preset light path interval;
    converting the polarization of said first light component into the polarization of said second light component, and converting the polarization of said second light component into the polarization of said first light component;
    bringing each of said next interfering light beams out of said light path interval;

mixing together said formed interfering light beams into a single beam of interfered light;

dividing said beam of interfered light into two beams having said independent polarizations;

recording an interference pattern formed in each of the divided light beams having a first known wavelength as follows:

converting the interfered light having the first of said independent polarizations into a first electric signal;

converting the interfered light having the second of said independent polarizations into a second electric signal;

measuring the phases of said electric signals;

changing the wavelength of coherent light at least once by a known value;

recording an interference pattern formed with each of the further known wavelengths, and measuring the phases of said first electric signal said second electric signal;

determining an integral part of the wavelengths within a preset light path interval from the relation between the phases of the electric signals measured at different known wavelengths of coherent light;

determining the optical length of a preset light path interval from the determined integral part of the wavelengths and from the measured phases of electric signals at the wavelength.

7. A digital multiple-beam laser interferometer, comprising:

a laser capable of emitting a beam of coherent light;

a device for separating from said light beam two collinear light components having mutually independent polarizations, said device being positioned past said laser along the run of the light beam;

a device for offsetting the frequency of one of said light components, said device being positioned past said laser as along the run of the light beam;

a master oscillator connected to said light frequency offsetting device;

at least two reflecting elements placed one after the other as along the run of the original light beam and adapted for presetting a light path interval and forming the interfering light beams by virtue of multiple reflection of the light beam from said reflecting elements;

a birefringent plate situated between said reflecting elements and adapted for mutual conversion of the polarizations of said light components;

a polarizing element arranged on the axis of said formed interfering light beams past said reflecting elements and adapted for splitting the light of said interfering beams into two interfered light beams having said mutually independent polarizations;

at least one photodetector located past said polarizing element on the axis of at least one of said interfered light beams and adapted for photoelectric conversion of the interfered light into an electric signal;

at least one phase measuring unit connected to the output of at least one said photodetector and adapted for measuring the phase of at least one said electric signal, from which phase the optical length of a preset light path interval is judged.

8. A laser interferometer as claimed in claim 7, wherein the light frequency offsetting device is an electro-optic frequency modulator.

9. A laser interferometer as claimed in claim 7, wherein the light frequency offsetting device is an acousto-optic frequency modulator.

10. A laser interferometer as claimed in claim 7, wherein said reflecting elements are made as partially reflecting mirror surfaces.

11. A laser interferometer as claimed in claim 7, wherein at least one of said reflecting elements is a diffraction grating.

12. A laser interferometer as claimed in claim 7, wherein at least one of said reflecting elements is a hologram.

13. A laser interferometer as claimed in claim 7, wherein said birefringent plate is a quarter-wave plate.

14. A laser interferometer as claimed in claim 11, wherein said birefringent plate features a difference between the phase shifts of light waves in two working diffraction orders equal to a quarter-wave-length.

15. A laser interferometer as claimed in claim 7, wherein said polarizing element is a polarizer.

16. A laser interferometer as claimed in claim 7, comprising at least two said photodetectors, a first and a second, wherein said polarizing element is a polarization beam-splitter adapted for dividing the light of the interfering beams into two said beams of interfered light, a first and a second, having linear mutually square polarizations, said first photodetector being set on the axis of said first interfered light beam and being connected to at least one of said phase measuring units, while the second photodetector is set on the axis of said second interfered light beam and is also connected to at least one of said phase measuring units.

17. A laser interferometer as claimed in claim 7, wherein said device for separating said two light components is adapted for forming two light components with circular polarizations featuring the opposite directions of rotation of the electric field vector.

18. A laser interferometer as claimed in claim 17, wherein used as the laser, the device for separating the light components with circular polarizations and the device for offsetting the light frequency is a dual-frequency laser.

19. A laser interferometer as claimed in claim 7, comprising a quarter-wave plate placed across the path of said interfering light beams before said polarizing element and adapted for converting circular light polarizations into linear ones, while the device for separating said two light components is adapted for forming two light components with linear mutually square polarizations.

20. A laser interferometer as claimed in claim 19, wherein the device for separating two light components with linear polarizations is a dual-beam polarization interferometer in one of whose beams said light frequency offsetting device is situated.

21. A digital multiple-beam laser interferometer, comprising:

a laser capable of emitting a beam of coherent light;

a device for separating from said light beam two collinear light components having mutually independent polarizations, said device being situated past said laser as along the run of the light beam;

a device for offsetting the frequency of one of said light components, said device being positioned past said laser along the run of the light beam;

a master oscillator connected to said light frequency offsetting device;

at least two reflecting elements placed one after the other along the run of the light beam and adapted for presetting a light path interval and forming a number of interfering light beams by virtue of multiple reflection of the light beam from said reflecting elements;

a birefringent plate situated between said reflecting elements and adapted for mutual conversion of said polarizations of said light components;

a beam-splitter element positioned between said light frequency offsetting device and said reflecting elements and adapted for separating said interfering beams reflected from said reflecting elements;

a polarizing element situated past said beam-splitter element along the run of said separated interfering beams and adapted for splitting the light of said separated interfering beams into two interfered light beams having said mutually independent polarizations;

at least one photodetector located past said polarizing element on the axis of at least one of said interfered light beams and adapted for photoelectric conversion of the interfered light into an electric signal;

at least one phase measuring unit connected to the output of at least one said photodetector and adapted for measuring the phase of at least one said electric signal so as to judge of the desired optical length of a preset light path interval by said phase.

22. A laser interferometer as claimed in claim 21, wherein said light frequency offsetting device is an electro-optic frequency modulator.

23. A laser interferometer as claimed in claim 21, wherein said light frequency offsetting device is an acousto-optic frequency modulator.

24. A laser interferometer as claimed in claim 21, wherein said reflecting elements are made as partially reflecting mirror surfaces.

25. A laser interferometer as claimed in claim 21, wherein at least one of said reflecting elements is a diffraction grating.

26. A laser interferometer as claimed in claim 21, wherein at least one of said reflecting elements is a hologram.

27. A laser interferometer as claimed in claim 21, wherein said birefringent plate is a quarter-wave plate.

28. A laser interferometer as claimed in claim 25, wherein said birefringent plate features a quarter-wave difference between the phase shifts of light waves in two working diffraction orders.

29. A laser interferometer as claimed in claim 21, wherein said polarizing element is a polarizer.

30. A laser interferometer as claimed in claim 21, comprising at least two said photodetectors, a first and a second, wherein said polarizing element is a polarization beam-splitter adapted for dividing the light of the interfering beams into two said interfered light beams, a first and a second, having linear mutually square polarizations, said first photodetector being set on the axis of said first interfered light beam and being connected to at least one of said phase measuring units, while the other of said photodetectors is set on the axis of said second interfered light beam and is also connected to at least one of said phase measuring units.

31. A laser interferometer as claimed in claim 21, wherein said device for separating said two light components is adapted for forming two light components having linear mutually square polarizations.

32. A laser interferometer as claimed in claim 31, wherein said device for separating said light components with linear independent polarizations is made as a dual-beam polarization interferometer, in one of whose beams said light frequency offsetting device is situated.

33. A laser interferometer as claimed in claim 21, comprising a quarter-wave plate put across the path of said separated interfering light beams past said beam-splitter element and adapted for converting circular light polarizations into linear ones, while the device for separating said two light components is adapted for forming two light components with circular polarizations having the opposite directions of rotation of the electric field vector.

34. A laser interferometer as claimed in claim 33, wherein used as said laser, said device for separating said light components with independent circular polarizations and said light frequency offsetting device is a dual-frequency laser.

35. A digital multiple-beam laser interferometer, comprising:

a laser capable of emitting a beam of coherent light;

a device for separating from said light beam two collinear light components having mutually independent polarizations, said device being situated past said laser along the run of the light beam;

a device for offsetting the light frequency of one of said light components, said device being situated past said laser along the run of the light beam;

a master oscillator connected to said light frequency offsetting device;

at least three reflecting elements positioned one after another as along the run of the light beam at the corners of a closed polygon and adapted for presetting a closed light path interval and for forming a number of interfering light beams by virtue of multiple reflection of the light beam from said reflecting elements;

a birefringent plate placed between said reflecting elements and adapted for mutual conversion of said polarizations of said light components;

a polarizing element placed on the axis of said formed interfering beams past said reflecting elements and adapted for dividing the light of said interfering beams into two interfered light beams having said mutually independent polarizations;

at least one photodetector situated past said polarizing element on the axis of at least one of said two interfered light beams and adapted for photoelectric conversion of the interfered light into an electric signal;

at least one phase measuring unit connected to the output of at least one said photodetector and adapted for measuring the phase of at least one said electric signal so as to judge of the desired optical length of a preset light path interval by said phase.

36. A laser interferometer as claimed in claim 35, wherein said device for light frequency offsetting is an electro-optic frequency modulator.

37. A laser interferometer as claimed in claim 35, wherein said light frequency offsetting device is an acousto-optic frequency modulator.

38. A laser interferometer as claimed in claim 35, wherein used as said laser, said device for separating said light components with mutually independent polarizations and said light frequency offsetting device is a dual-frequency laser.

39. A laser interferometer as claimed in claim 35, wherein said device for separating said light components with mutually independent polarizations is made as a dual-beam polarization interferometer in one of whose beams said light frequency offsetting device is situated.

40. A laser interferometer as claimed in claim 35, wherein said reflecting elements are made as partially reflecting mirror surfaces.

41. A laser interferometer as claimed in claim 35, wherein at least one of said reflecting elements is a diffraction grating.

42. A laser interferometer as claimed in claim 35, wherein at least one of said reflecting elements is a hologram.

43. A laser interferometer as claimed in claim 35, wherein said birefringent plate is a quarter-wave plate located close to one of said reflecting elements.

44. A laser interferometer as claimed in claim 41, wherein said birefringent plate is located close to said diffraction grating and features a quarter-wave difference between the phase shifts of light waves in two working diffraction orders.

45. A laser interferometer as claimed in claim 35, wherein said birefringent plate is a half-wave plate.

46. A laser interferometer as claimed in claim 35, wherein said polarizing element is a polarizer.

47. A laser interferometer as claimed in claim 35, comprising at least two said photodetectors, a first and a second, wherein said polarizing element is a polarization beam-splitter adapted for dividing the light of the interfering beams into two said beams, a first and a second, having linear mutually square polarizations, said first photodetector being set on the axis of said first interfered light beam and being connected to at least one said phase measuring unit, while the second of said photodetectors is arranged on the axis of said second separated beam of interfered light and is also connected to at least one said phase measuring unit.

48. A digital multiple-beam laser interferometer, comprising:
- a laser capable of emitting a beam of coherent light;
- a device for separating from said light beam two collinear light components having mutually independent polarizations, said device being situated past said laser as along the run of the light beam;
- a device for offsetting the light frequency of one of said light components, said device being situated past said laser along the run of the light beam;
- a master oscillator connected to said light frequency offsetting device;
- an optical system adapted for expanding an original light beam and located past the light frequency offsetting device;
- at least two reflecting elements placed one after the other along the run of the light beam and adapted for presetting a light path interval and for forming a number of interfering beams by virtue of multiple reflection of the light beam from said reflecting elements;
- a birefringent plate placed between said reflecting elements and adapted for mutual conversion of said polarizations of said light components;
- a polarizing element positioned on the axis of said formed interfering beams past said reflecting elements and adapted for dividing the light of said interfering beams into two interfered light beams having said mutually independent polarizations;
- at leeast one photoelectric converter of interfered light into an electric signal, located past said polarizing element on the axis of at least one of said two interfered light beams;
- at least one phase measuring unit connected to the output of at least one of said photoelectric converters and adapted for measuring the phase of at least one said electric signal so as to judge of the desired optical length of a light path interval by said phase.

49. A laser interferometer as claimed in claim 48, wherein said light frequency offsetting device is an electro-optic frequency modulator.

50. A laser interferometer as claimed in claim 48, wherein said light frequency offsetting device is an acousto-optic frequency modulator.

51. A laser interferometer as claimed in claim 48, wherein used as said laser, said device for separating said light components with mutually independent polarizations and said light frequency offsetting device is a dual-frequency laser.

52. A laser interferometer as claimed in claim 48, wherein said device for separating said light components with mutually independent polarizations is made as a dual-beam polarization interferometer in one of whose beams said light frequency offsetting device is situated.

53. A laser interferometer as claimed in claim 48, wherein said reflecting elements are made as partially reflecting mirror surfaces.

54. A laser interferometer as claimed in claim 48, wherein at least one of said reflecting elements is a diffraction grating.

55. A laser interferometer as claimed in claim 48, wherein at least one of said reflecting elements is a hologram.

56. A laser interferometer as claimed in claim 48, wherein said birefringent plate is a quarter-wave plate.

57. A laser interferometer as claimed in claim 54, wherein said birefringent plate features a quarter-wave difference between the phase shifts of light waves in two working diffraction orders.

58. A laser interferometer as claimed in claim 48, wherein said polarizing element is a polarizer.

59. A laser interferometer as claimed in claim 48, comprising at least two said photoelectric converters, a first and a second, wherein said polarizing element is a polarization beam-splitter adapted for dividing the light of the interfering beams into two said beams, a first and a second, of interfered light with linear mutually square polarizations, the first of said photoelectric converters being arranged on the axis of said first interfered light beam and being connected to at least one said phase measuring unit, while the second of said photoelectric converters is arranged on the axis of said second interfered light beam and is also connected to at least one said phase measuring unit.

60. A laser interferometer as claimed in claim 48, wherein said photoelectric converter is a quadratic photodetector.

61. A laser interferometer as claimed in claim 48, wherein said photoelectric converter is a photodetector array whose photodetectors are connected to the phase measuring unit through a switching device.

62. A laser interferometer as claimed in claim 48, wherein said photoelectric converters is a photodetector array, each of said photodetectors being connected to its own phase measuring unit.

63. A laser interferometer as claimed in claim 48, comprising a scanning device connected to at least one said photoelectric converter and adapted for converting the interfered light at different points across the interfering light beams.

64. A digital multiple-beam laser interferometer adapted for measuring the distribution of the light path optical length, comprising:
   a laser capable of emitting a beam of coherent light;
   a device for separating from said light beam two collinear light components having mutually independent polarizations, said device being located past said laser along the run of the light beam;
   a device for offsetting the light frequency of one of said light components, said device being located past said laser along the run of the light beam;
   a master oscillator connected to said light frequency offsetting device;
   a device for displacing the original light beam parallel to itself in two mutually square directions, said device being located past the light frequency offsetting device along the run of the light beam;
   a least two reflecting elements positioned one after the other as along the run of the light beam and adapted for presetting a light path interval and for forming a number of intefering light beams by virtue of multiple reflection of said light beam;
   a birefringent plate positioned between said reflecting elements and adapted for mutual conversion of said mutually independent polarizations of said light components;
   a polarizing elements arranged on the axis of said formed interfering beams past said reflecting elements and adapted for dividing the light of said interfering light beams into two interfered light beams with said mutually independent polarizations;
   at least one photoelectric converter of interfered light into an electric signal, said converter being located past said polarizing element on the axis of at least one of said two beams of interfered light;
   at least one phase measuring unit connected to the output of at least one of said photoelectric converters and adapted for measuring the phase of at least one said electric signal so as to judge of the distribution on the desired light path optical length by said phase.

65. A laser interferometer as claimed in claim 64, wherein said light frequency offsetting device is an electro-optic frequency modulator.

66. A laser interferometer as claimed in claim 64, wherein said light frequency offsetting device is an acousto-optic frequency modulator.

67. A laser interferometer as claimed in claim 64, wherein used as said laser, said device for separating said light components with mutually independent polarizations and said light frequency offsetting device is a dual-frequency laser.

68. A laser interferometer as claimed in claim 64, wherein said device for separating said light components with mutually independent polarizations is made as a dual-beam polarization interferometer in one of whose beams said light frequency offsetting device is situated.

69. A laser interferometer as claimed in claim 64, wherein said reflecting elements are made as partially reflecting mirror surfaces.

70. A laser interferometer as claimed in claim 64, wherein at least one of said reflecting elements is a diffraction grating.

71. A laser interferometer as claimed in claim 64, wherein at least one of said reflecting elements is a hologram.

72. A laser interferometer as claimed in claim 64, wherein said birefringent plate is a quarter-wave plate.

73. A laser interferometer as claimed in claim 70, wherein said birefringent plate features a quarter-wave difference between the phase shifts of light waves in two working diffraction orders.

74. A laser interferometer as claimed in claim 64, wherein said polarizing element is a polarizer.

75. A laser interferometer as claimed in claim 64, comprising at least two said photoelectric converters, a first and a second, wherein said polarizing element is a polarization beam-splitter adapted for dividing the light of the interfering beams into two beams, a first and a second, of interfered light with linear mutually square polarizations, the first of said photoelectric converters being arranged on the axis of said first interfered light beam and being connected to at least one said phase measuring unit, while the second of said photoelectric converters is arranged on the axis of said second interfered light beam and is also connected to at least one said phase measuring unit.

76. A laser interferometer as claimed in claim 64, wherein said photoelectric converter is a quadratic photodetector.

77. A laser interferometer as claimed in claim 76, comprising converging lens located before said photodetector and adapted for continuously directing the beam of interfered light to said photodetector as the original light beam is being displaced parallel to itself.

78. A laser interferometer as claimed in claim 76, comprising a scanning device connected to said photodetector and linked to said device for displacing the original light beam parallel to itself, said scanning device being adapted for providing a possibility of converting the interfered light as the original light beam is being displaced parallel to itself.

79. A laser interferometer as claimed in claim 64, wherein said photoelectric converter is a photodetector array whose photodetectors are connected to the phase measuring unit through a switching device linked to said device for displacing the original light beam parallel to itself.

80. A digital multiple-beam laser interferometer, comprising:
   a laser capable of emitting a beam of coherent light;
   a device for separating from said light beam two collinear light components with mutually independent polarizations, said device being located past said laser along the run of the light beam;
   a device for offsetting the light frequency of one of said light components, said device being located past said laser along the run of the light beam;
   a master oscillator connected to said light frequency offsetting device;
   an optical system adapted for expanding the original light beam and located past the light frequency offsetting device;
   at least two reflecting elements positioned one after the other along the run of the light beam and adapted for presetting a light path interval and for forming a number of interfering light beams by virtue of multiple reflection of said light beam;

a birefringent plate located between said reflecting elements and adapted for mutual conversion of said independent polarizations of said light components;

an optical element arranged on the axis of said formed interfering beams past said reflecting elements and adapted for separating part of the light of the interfering beams;

a first polarizing element arranged on the axis of said interfering light beams past said optical element and adapted for splitting the light of said interfering light beams into two beams, a first and a second, of interfered light with said mutually independent polarizations;

a second polarizing element arranged on the axis of the beam of said separated part of the light of the interfering light beams past said optical element and adapted for dividing the light of said beam of separated part of light into two beams, a third and a fourth, of interfered light with said mutually independent polarizations;

at least one main photoelectric converter of interfered light into an electric signal, said main photoelectric converter being located past said first polarizing element at no less than one preset point across at least one of said two, the first and the second, beams of interfered light;

at least one additional photoelectric converter of interfered light into an electric signal, said additional photoelectric converter being located past said second polarizing element at no less than one reference point across at least one of said two, the third and the fourth, beams of interfered light;

at least one main phase measuring unit connected to the output of at least one said main photoelectric converter and adapted for measuring the phase of at least one said electric signal so as to judge of the optical length of a preset light path interval at no less than one said preset point across said light beam by said measured phase;

at least one additional phase measuring unit connected to the output of at least one said additional photoelectric converter and adapted for measuring the phase of at least one said electric signal so as to judge of the optical length of a preset light path interval by said measured phase, at no less than one said preset reference points across said light beam.

81. A laser interferometer as claimed in claim 80, wherein at least one said main phase measuring unit is also connected to the output of at least one additional photoelectric converter, and a ratio of the optical lengths of the light path interval at no less than one preset point and at no less than one reference point across said light beam is judged by the phase value as measured by said phase measuring unit.

82. A laser interferometer as claimed in claim 80, comprising a scanning device connected to at least one main photoelectric converter.

83. A laser interferometer as claimed in claim 80, wherein said light frequency offsetting device is an electro-optic frequency modulator.

84. A laser interferometer as claimed in claim 80, wherein said light frequency offsetting device is an acousto-optic frequency modulator.

85. A laser interferometer as claimed in claim 80, wherein used as said laser, said device for separating said light components with mutually independent circular polarizations and said light frequency offsetting device is a dual-frequency laser.

86. A laser interferometer as claimed in claim 80, wherein said device for separating said light components is made as a dual-beam polarization interferometer in one of whose beams said light frequency offsetting device is situated.

87. A laser interferometer as claimed in claim 80, wherein said reflecting elements are made as partially reflecting mirror surfaces.

88. A laser interferometer as claimed in claim 80, wherein at least one of said reflecting elements is a diffraction grating.

89. A laser interferometer as claimed in claim 80, wherein at least one of said reflecting elements is a hologram.

90. A laser interferometer as claimed in claim 80, wherein said birefringent plate is a quarter-wave plate.

91. A laser interferometer as claimed in claim 88, wherein said birefringent plate features a quarter-wave difference between the phase shifts of light waves in two working diffraction orders.

92. A laser interferometer as claimed in claim 80, wherein said first polarizing element is a polarizer.

93. A laser interferometer as claimed in claim 80, wherein said second polarizing element is a polarizer.

94. A laser interferometer as claimed in claim 80, comprising at least two said main photoelectric converters, a first and a second, wherein said first polarizing element is a polarization beam-splitter adapted for dividing the light of the interfering beams into two beams, a first and a second, of interfered light with linear mutually square polarizations, the first of said photoelectric converters being arranged on the axis of said first beam of interfered light and being connected to at least one said phase measuring unit, while the second of said photoelectric converters is arranged on the axis of said second beam of interfered light and is also connected to at least one said phase measuring unit.

95. A laser interferometer as claimed in claim 80, wherein said main photoelectric converter is a quadratic photodetector.

96. A laser interferometer as claimed in claim 80, wherein said additional photoelectric converter is a quadratic photodetector.

97. A laser interferometer as claimed in claim 80, wherein said main photoelectric converter is a photodetector array whose photodetectors are connected to said main phase measuring unit via a switching device.

98. A laser interferometer as claimed in claim 80, wherein said main photoelectric converter is made as a photodetector array, each of the photodetectors of said array being connected to its own phase measuring unit.

99. A laser interferometer as claimed in claim 80, wherein said additional photoelectric converter is a photodetector array whose photodetectors are connected to said additional phase measuring unit through a switching device.

100. A laser interferometer as claimed in claim 80, wherein said additional photoelectric converter is in fact a photodetector array, each of the photodetectors of said array being connected to its own phase measuring unit.

101. a digital multiple-beam laser interferometer, comprisng:
a laser capable of emitting a beam of coherent light;
a device for separating from said light beam two collinear light components with mutually independent polarizations, said device being located past said laser along the run of the light beam;

a device for offsetting the light frequency of one of said light components, said device being located past said laser along the run of the light beam;

a master oscillator connected to said light frequency offsetting device;

at least two reflecting elements positioned one after the other along the run of the light beam and adapted for presetting a light path interval and for forming a number of interfering light beams by virtue of multiple reflection of said light beam from said reflecting elements;

a birefringent plate located between said reflecting elements and adapted for mutual conversion of said independent polarizations of said light components;

at least one device for changing the optical length of light path within a preset interval, said device being located between said reflecting elements and adapted for controlled variation of the light path optical length along at least one ray in a light beam;

at least one transducer for sensing a change in the light path optical length, said transducer being connected to said device for changing the light path optical length;

a polarizing element arranged on the axis of said formed interfering beams past said reflecting elements along the run of the light beam and adapted for dividing the light of said interfering beams into two beams of interfered light with said mutually independent polarizations;

at least one photodetector located past said polarizing element on the axis of at least one of said two beams of interfered light and adapted for photoelectric conversion of the interfered light into an electric signal;

at least one phase measuring unit connected to the output of at least one of said photodetectors and adapted for measuring the phase of at least one said electric signal;

at least one phase value presetting unit adapted for presetting phase values corresponding to the known values of the light path optical length;

at least one phase comparator unit whose inputs are connected to at least one said phase measuring unit and to at least one said phase value presetting unit, while the output of said phase comparator unit is connected to at least one said device for changing the light path optical length, said phase comparator unit being adapted for comparing the measured phase value with a preset value thereof, generating an error signal dependent upon the results of phase comparison and controlling, by means of said error signal, a change in the light path optical length along at least one ray of a light beam;

a computer device connected to the outputs of at least one said phase measuring unit and of at least one said transducer for sensing a change in the light path optical length, said computer device being adapted for determining the desired optical length of a preset light path interval from the results of measurement of the phases of electric signals and from the value of a change in the light path optical length.

102. A laser interferometer as claimed in claim 101, wherein at least one said phase value presetting unit is also connected to the output of at least one said phase measuring unit.

103. A laser interferometer as claimed in claim 101, wherein used as at least one said phase value presetting unit, as at least one said phase comparator unit and as said computer device is a computer whose inputs are connected to the outputs of at least one said phase measuring unit and of at least one said transducer for sensing a change in the light path optical length, while the control output of said computer is connected to at least one said device for changing the light path optical length.

104. A laser interferometer as claimed in claim 101, wherein said device for changing the light path optical length is a knonw-length hermetically sealed cell filled with a known gas and placed between said reflecting elements, and a compressor connected to said cell, while said transducer for sensing a change in the light path optical length is in fact a pressure transducer.

105. A laser interferometer as claimed in claim 101, wherein said device for changing the light path optical length is a known-length cell made from a known optical material and placed between said reflecting elements, and a heater element having thermal contact with said cell, while said transducer for sensing a change in the light path optical length is in fact a temperature sensor.

106. A laser interferometer as claimed in claim 101, wherein said light frequency offsetting device is an electro-optic frequency modulator.

107. A laser interferometer as claimed in claim 101, wherein said light frequency offsetting device is an acousto-optic frequency modulator.

108. A laser interferometer as claimed in claim 101, wherein used as said laser of the device for separating said light components with mutually independent circular polarizations and of the light frequency offsetting device is a dual-frequency laser.

109. A laser interferometer as claimed in claim 101, wherein said device for separating said light components is made as a dual-beam polarization interferometer in one of whose beams said light frequency offsetting device is situated.

110. A laser interferometer as claimed in claim 101, wherein said reflecting elements are made as partially reflecting mirror surfaces.

111. A laser interferometer as claimed in claim 101, wherein at least one of said reflecting elements is a diffraction grating.

112. A laser interferometer as claimed in claim 101, wherein at least one of said reflecting elements is a hologram.

113. A laser interferometer as claimed in claim 101, wherein said birefringent plate is a quarter-wave plate.

114. A laser interferometer as claimed in claim 111, wherein said birefringent plate features a quarter-wave difference between the phase shifts of light waves in two working diffraction orders.

115. A laser interferometer as claimed in claim 101, wherein said polarizing element is a polarizer.

116. A laser interferometer as claimed in claim 101, comprising at least two said photodetectors, a first and a second, wherein said polarizing element is in effect a polarization beam-splitter adapted for dividing the light of the interfering beams into two said beams, a first and a second, of interfered light with linear mutually square polarizations, the first of said photodetectors being arranged on the axis of said first beam of interfered light and being connected to at least one said phase measuring unit, while the second of said photodetectors is arranged on the axis of said second beams of interfered light and is also connected to at least one said phase measuring unit.

117. A digital multiple-beam laser interferometer capable of simultaneous visual observation of an interference pattern, said interferometer comprising:
a laser capable of emitting a beam of coherent light;
a device for separating from said light beam two collinear light components with mutually independent polarizations, said device being located past said laser along the run of the light beam;
a device for offsetting the light frequency of one of said light components, said device being located past said laser along the run of the light beam;
a master oscillator connected to said light frequency offsetting device;
an optical system for expanding the light beam, said system being located past the light frequency offsetting device;
at least two reflecting elements arranged one after the other as along the run of the light beam and adapted for presetting a light path interval and for forming a number of interfering light beams by virtue of multiple reflection of the light beam from said reflecting elements;
a birefringent plate located between said reflecting elements and adapted for mutual conversion of said polarizations of said light components;
a beam-splitter element located between said light frequency offsetting device on the one side and said reflecting elements on the other side and adapted for separating the interfering light beams reflected from said reflecting elements;
a polarizing element located past said beam-splitter element along the run of said reflected interfering light beams;
at least one photoelectric converter of the interfered light into an electric signal, said converter being located past said polarizing element on the axis of at least one of said two beams of interfered light;
at least one phase measuring unit connected to the output of at least one said photoelectric converter and adapted for measuring the phase of at least one said electric signal so as to judge of the desired optical length of a preset light path interval by said phase;
an optical beam-splitter element located on the axis of the interfering light beams between said reflecting elements on the one side and at least one said photoelectric converter on the other side and adapted for separating part of the light of the interfering beams for visual observation of the interference pattern;
a light intensity modulator located past said optical beam-splitter element on the axis of the beam of the separated part of light of the interfering light beams and adapted for the separated part of light of the interfering light beams to pass at preset short time intervals;
an interference pattern image recorder located past said light intensity modulator along the run of the beam of the separated part of light of the interfering beams and adapted for recording or visually observing the resulting interference pattern;
a pulse generator connected to said light intensity modulator and adapted for controlling said modulator by setting electric pulses within said short time intervals.

118. A laser interferometer as claimed in claim 117, wherein with the purpose of establishing a static interference pattern by gating the beam of separated light of the interfering beams, said pulse generator is connected to the output of said master oscillator.

119. A laser interferometer as claimed in claim 117, wherein with the purpose of establishing a static interference pattern, said pulse generator is connected to the output of at least one said photoelectric converter.

120. A laser interferometer as claimed in claim 117, wherein said light frequency offsetting device is an electro-optic frequency modulator.

121. A laser interferometer as claimed in claim 117, wherein said light frequency offsetting device is an acousto-optic frequency modulator.

122. A laser interferometer as claimed in claim 117, wherein used as said laser of the device for separating said light components with mutually independent polarizations and of the light frequency offsetting device is a dual-frequency laser.

123. A laser interferometer as claimed in claim 117, wherein said device for separating said light components with mutually independent polarizations is made as a dual-beam polarization interferometer in one of whose beams said light frequency offsetting device is situated.

124. A laser interferometer as claimed in claim 117, wherein said reflecting elements are made as partially reflecting mirror surfaces.

125. A laser interferometer as claimed in claim 117, wherein at least one of said reflecting elements is a diffraction grating.

126. A laser interferometer as claimed in claim 117, wherein at least one of said reflecting elements is a hologram.

127. A laser interferometer as claimed in claim 117, wherein said birefringent plate is a quarter-wave plate.

128. A laser interferometer as claimed in claim 125, wherein said birefringent plate features a quarter-wave difference between the phase shifts of light waves in two working diffraction orders.

129. A laser interferometer as claimed in claim 117, wherein said polarizing element is a polarizer.

130. A laser interferometer as claimed in claim 117, comprising at least two said photoelectric converters, a first and a second, wherein said polarizing element is a polarization beam-splitter adapted for dividing the light of the interfering beams into two said beams, a first and a second, of interfered light with linear mutually square polarizations, the first of said photoelectric converters being arranged on the axis of said first beam of interfered light and being connected to at least one said phase measuring phase, while the second of said photoelectric converters is arranged on the axis of said second beam of interfered light and is also connected to at least one said phase measuring unit.

131. A laser interferometer as claimed in claim 117, wherein said photoelectric converter is a photodetector array whose photodetectors are connected to the phase measuring unit through a switching device.

132. A laser interferometer as claimed in claim 117 wherein said photoelectric converter is a photodetector array whose photodetectors are connected to the phase measuring unit through a switching device.

133. A laser interferometer as claimed in claim 117, wherein said photoelectric converter is made as a photodetector array, each of whose photodetectors is connected to its own phase measuring unit.

134. A laser interferometer as claimed in claim 117, comprising a scanning device connected to at least one said photoelectric converter and adapted for providing a possibility of converting the interfered light at different points across the interfering beams.

135. A digital multiple-beam laser interferometer, comprising:
- a laser capable of emitting a beam of coherent light having different wavelengths;
- a device for separating from said light beam two collinear light components with mutually independent polarizations, said device being located past said laser along the run of the light beam;
- a device for offsetting the light frequency of one of said light components, said device being located past said laser along the run of the light beam;
- a master oscillator connected to said light frequency offsetting device;
- at least two reflecting elements positioned one after the other along the run of the light beam and adapted for presetting a light path interval and for forming a plurality of interfering light beams by virtue of multiple reflection of the light beam from said reflecting elements;
- a birefringent plate located between said reflecting elements and adapted for mutual conversion of said polarizations of said light components;
- a beam-splitter element located between said light frequency offsetting device on the one side and said reflecting elements on the other side and adapted for separating said interfering light beams reflected from said reflecting elements;
- a polarizing element located past said beam-splitter element along the run of said separated interfering light beams and adapted for dividing the light of said interfering beams into two beams of interfered light with said independent polarizations;
- at least one photoelectric converter of the interfered light into an electric signal, said converter being located past said polarizing element on the axis of at least one of said two beams of interfered light;
- at least one phase measuring unit connected to the output of at least one said photoelectric converter and adapted for measuring the phase of said electric signal so as to judge of the desired optical length of a preset light path interval by said phase;
- a computer device connected to the output of at least one said phase measuring unit and to said laser and adapted for calculating an integral and a fraction part of the periods of the desired value of the optical length of a preset light path interval from the results of measuring the phases of electric signals at different known values of said laser wavelengths.

136. A laser interferometer as claimed in claim 135, wherein said laser features a tunable wavelength.

137. A laser interferometer as claimed in claim 135, comprising an optical unit adapted for splitting the beam of interfered light into a number of separate beams depending upon the light wavelength, said optical unit being located between said polarizing element and at least one said photoelectric converter as along the run of the beam of interfered light so that arranged on the axis of each of said separated beams is at least one photoelectric converter connected to its own phase measuring unit, while the laser emits light of at least two wavelengths at a time.

138. A laser interferometer as claimed in claim 135, wherein said light frequency offsetting device is an electrooptic frequency modulator.

139. A laser interferometer as claimed in claim 135, wherein said light frequency offsetting device is an acousto-optic frequency modulator.

140. A laser interferometer as claimed in claim 135, wherein used as said laser, said device for separating said light components with mutually independent polarizations and said light frequency offsetting device is a dual-frequency laser.

141. A laser interferometer as claimed in claim 135, wherein said device for separating said light components with mutually independent polarizations is made as a dual-beam polarization interferometer in one of whose beams said light frequency offsetting device is situated.

142. A laser interferometer as claimed in claim 135, wherein said reflecting elements are made as partially reflecting mirror surfaces.

143. A laser interferometer as claimed in claim 135, wherein at least one of said reflecting elements is a diffraction grating.

144. A laser interferometer as claimed in claim 135, wherein at least one of said reflecting elements is made as a hologram.

145. A laser interferometer as claimed in claim 135, wherein said birefringent plate is a quarter-wave plate.

146. A laser interferometer as claimed in claim 143, wherein said birefringent plate features a quarter-wave difference between the phase shifts of light waves in two working diffraction orders.

147. A laser interferometer as claimed in claim 135, wherein said polarizing element is a polarizer.

148. A laser interferometer as claimed in claim 135, comprising at least two said photoelectric converters, a first and a second, wherein said polarizing element is a polarization beam-splitter adapted for dividing the light of the interfering beams into two said beams, a first and a second, of interfered light with linear mutually square polarizations, the first of said photoelectric converters being arranged on the axis of said first beam of interfered light and being connected to at least one said phase measuring unit, while the second of said photoelectric converters is arranged on the axis of said second beam of interfered light and is also connected to at least one said phase measuring unit.

149. A laser interferometer as claimed in claim 135, wherein said photoelectric converter is a quadratic photodetector.

150. A laser interferometer as claimed in claim 135, wherein said photoelectric converter is a photodetector array whose photodetectors are connected to the phase measuring unit through a switching device.

151. A laser interferometer as claimed in claim 135, wherein said photoelectric converter is a photodetector array, each of whose photodetectors is connected to its own phase measuring unit.

152. A laser interferometer as claimed in claim 135, comprising a scanning device connected to at least one said photoelectric converter and adapted for providing a possibility of converting the interfered light at different points across the interfering beams.

* * * * *